(12) United States Patent
Vera-Portocarrero et al.

(10) Patent No.: US 11,534,597 B2
(45) Date of Patent: Dec. 27, 2022

(54) STIMULATION RESPONSE PROFILES

(71) Applicant: Medtronic, Inc., Minneapolis, MN (US)

(72) Inventors: Louis P. Vera-Portocarrero, St. Anthony, MN (US); Nathan A. Torgerson, Andover, MN (US); Melanie D. Goodman Keiser, Otsego, MN (US)

(73) Assignee: Medtronic, Inc., Minneapolis, MN (US)

( * ) Notice: Subject to any disclaimer, the term of this patent is extended or adjusted under 35 U.S.C. 154(b) by 120 days.

(21) Appl. No.: 16/879,297

(22) Filed: May 20, 2020

(65) Prior Publication Data

US 2020/0368518 A1 Nov. 26, 2020

Related U.S. Application Data

(60) Provisional application No. 62/851,726, filed on May 23, 2019.

(51) Int. Cl.
| | |
|---|---|
| A61N 1/02 | (2006.01) |
| G16H 20/30 | (2018.01) |
| A61N 1/36 | (2006.01) |
| A61N 1/372 | (2006.01) |

(52) U.S. Cl.
CPC .......... A61N 1/025 (2013.01); A61N 1/36071 (2013.01); A61N 1/36128 (2013.01); A61N 1/37211 (2013.01); G16H 20/30 (2018.01); *A61N 1/3603* (2017.08); *A61N 1/36021* (2013.01)

(58) Field of Classification Search
CPC ............... A61N 1/025; G16H 20/30
USPC ................................................. 607/46
See application file for complete search history.

(56) References Cited

U.S. PATENT DOCUMENTS

| | | | |
|---|---|---|---|
| 10,076,664 | B1 | 9/2018 | Thacker et al. |
| 2014/0378941 | A1* | 12/2014 | Su .............. A61M 5/1723 604/506 |
| 2016/0213314 | A1 | 7/2016 | Zuckerman-stark et al. |
| 2019/0111266 | A1 | 4/2019 | Kaemmerer et al. |

FOREIGN PATENT DOCUMENTS

WO 2018080653 A1 5/2018

OTHER PUBLICATIONS

Wilkes, "A large animal neuropathic pain model in sheep: a strategy for improving the predictability of preclinical models for therapeutic development", Journal of Pain Research, Oct. 24, 2012, pp. 415-424.

International Search Report and Written Opinion of International Application No. PCT/US2020/033926, dated Aug. 14, 2020, 13 pp.

* cited by examiner

*Primary Examiner* — Nadia A Mahmood
(74) *Attorney, Agent, or Firm* — Shumaker & Sieffert, P.A.

(57) ABSTRACT

Techniques for providing therapy to a patient via electrical stimulation are described. The techniques include, for example, determining, relative to a start time of providing the electrical stimulation, one or more efficacy times that correspond to an efficacy indicator, determining, according to the efficacy times, efficacy data items for the patient, comparing the efficacy data items with the efficacy indicator, and generating, based on the comparison, a prediction of an expected response to the therapy manifesting in the patient at a prospective time.

19 Claims, 13 Drawing Sheets

STIMULATION RESPONSE PROFILES

This application claims the benefit of U.S. Provisional Patent Application No. 62/851,726, entitled STIMULATION RESPONSE PROFILES, filed May 23, 2019, the entirety of which is hereby incorporated by reference.

FIELD

The disclosure relates to electrical stimulation therapy.

BACKGROUND

Various medical devices, including implantable medical device (IMDs), have been proposed for use in different therapeutic applications, such as deep brain stimulation (DBS), spinal cord stimulation (SCS), pelvic stimulation, gastric stimulation, peripheral nerve field stimulation (PNFS), and functional electrical stimulation. These medical devices, in various examples, include electrical stimulators, therapeutic agent delivery devices, etc. In some therapy systems, an implantable electrical stimulator delivers electrical stimulation (e.g., electrical stimulation therapy, electrical stimulation treatment, etc.) to a target tissue site within a patient with the aid of one or more electrodes. In some examples, the one or more electrodes may be deployed on a housing of the electrical stimulator, by one or more medical leads, or deployed by the one or more medical leads, as well as on the housing.

During a programming session, which may occur during implant of the medical device, during a trial session, or during an in-clinic or remote follow-up session after the medical device is implanted in a patient, a clinician may generate one or more therapy programs (also referred to as a set of therapy parameters or simply a therapy parameter set) that provide potentially efficacious therapy to the patient. Each therapy program may define values for the set of therapy parameters. A medical device may deliver therapy to the patient according to one or more therapy programs. In the case of electrical stimulation, the therapy parameters may define characteristics of an electrical stimulation waveform to be delivered.

SUMMARY

In general, the disclosed technology relates to systems, devices, and techniques for generating a prediction as to whether a particular patient is likely to respond positively to a particular therapy program for a prolonged period of time. As such, a result of the prediction may indicate that the therapy program is likely to provide a particular degree of long-term efficacy for the particular patient. In generating the prediction, a long-term efficacy indicator may be selected that corresponds to characteristics of the particular therapy program. The long-term efficacy indicator may indicate particular times in which the particular therapy program is likely to provide particular reproducible effects that, if observed in a current patient at the particular efficacy times, would indicate a high likelihood of long-term efficacy, even where, at other times, the patient has a negative response to the therapy.

In an example, a prediction generator may obtain efficacy data that indicates how the patient is currently responding to the particular therapy program. The efficacy data may include response variables, such as pain scores, withdrawal thresholds, or other data items that indicate how the patient is responding to the particular therapy program at various moments in time. In an example, the efficacy data may include a patient pain score that represents a particular level of pain relief perceived by the patient at a moment in time following an initiation of the therapy program. When such efficacy data is collected and arranged chronologically, the efficacy data represents a response profile. As such, efficacy data of a current patient generally represents a short-term response profile of the current patient. In accordance with techniques of the disclosure, a prediction generator may compare the long-term efficacy indicator determined for the particular therapy program with efficacy data items of the short-term response profile.

The long-term indicator of efficacy (e.g., an efficacy indicator) may include one or more of a predetermined response profile, one or more historical response profiles, response indicators, efficacy markers, baseline thresholds, etc. The long-term efficacy indicator may define a timeframe that extends beyond that of a current treatment of a patient. That is, the efficacy indicator may, in some instances, effectively represent a greater number of data points compared to that of the short-term response profile of a patient.

In addition, the efficacy indicators identify particular efficacy times in which historical responses from other patients may have exhibited particular identifiable behaviors, such as predictable fluctuating patterns at certain points in time relative to a start time of a particular therapy. That is, the efficacy indicator may include one or more known indicators of long-term efficacy for particular therapies, such as initial positive responses, initial negative responses prior to or following an initial positive response, etc.

In such examples, a prediction generator may develop a short-term response profile for a patient by prompting for efficacy data from the patient or device associated with the patient at the specific efficacy times defined by the efficacy indicator. The developing response profile for a patient may generally track how a patient appears to be responding to a therapy at particular points in time as defined by efficacy data items obtained from the patient at those particular points in time. A developing response profile invariably includes gaps in the data collection set that, for example, may be based on time constraints of a physician or patient. That is, certain efficacy data items, such as pain level evaluations, may not be feasibly obtained at all points in time for a particular therapy session and thus, efficacy data items may be collected on a somewhat arbitrary schedule that may not necessarily include particular times that otherwise may be defined by an efficacy indicator as in the disclosure.

As described herein, when certain gaps are closed by measurement efficacy data of response variables, the developing response profile may then ultimately include a sufficient amount and/or alignment of efficacy data items, such that a prediction generator may conclude that the therapy is likely to provide a term of efficacious results for the patient that extends to prospective times. On the other hand, in the presence of certain gaps, such as gaps corresponding to one or more of the determined efficacy times, a prediction generator may be unable to provide a prediction determination or in some instances, may generate a prediction while including a provision that the prediction likely suffers from a low confidence interval due to the one or more gaps in efficacy data.

The aforementioned issues, among others, may be addressed by the disclosed techniques that include first determining, for a particular therapy program, a long-term efficacy indicator that corresponds to various characteristics of a therapy program. A prediction generator, implemented by one or more processors, may utilize the efficacy indicator to determine efficacy times and may predict an efficacy of the particular therapy program based on data items determined in accordance with the efficacy times. Specifically, the prediction generator may determine, from an efficacy indicator, one or more efficacy times, which may include one or more time windows determined based on various characteristics of the efficacy indicator. Particular aspects relate to identifying positive responders of a therapy program by correlating the efficacy data items of the patient to characteristics of an efficacy indicator, such as characteristics that correspond to the efficacy times. Such correlation can be particularly useful for reducing false negatives, such as might otherwise occur when a short- or mid-term response shows a reduction in the response criteria.

The prediction generator may output an indication as to the efficacy times, which may indicate criteria for collecting efficacy data items at particular efficacy times and/or for retrospectively evaluating a particular set of efficacy data items that correspond to the efficacy times. The prediction generator may then generate a prediction of long-term efficacy for the therapy by comparing the efficacy indicator with the efficacy data items collected and/or evaluated in accordance with the determined efficacy times. In an illustrative example, a prediction of long-term positive results may include a prediction that a patient may experience pain relief, such as general pain relief or other quantifiable amount of pain relief, at a prospective time relative to a start of receiving the electrical stimulation treatment determined for the patient. In some examples, the prediction may include an indication that the patient is expected to experience pain relief for a predetermined amount of time, such as an amount of time forecasted to a future period of time.

In some examples, the efficacy prediction may include information as to whether a particular therapy program determined for the patient is likely or otherwise is unlikely to provide long-term positive results for the patient and/or whether a different therapy program may provide a higher likelihood of positive results for the patient. In such examples, a prediction generator or therapy adjuster, implemented in processing circuitry, may automatically determine a therapy program in response to comparing efficacy data items (e.g., a developing short-term response profile of the patient) with the long-term efficacy indicator. In some examples, particular efficacy data items and/or prediction results may serve as input for determining an adjustment to the therapy, such as when the prediction generator determines the likelihood of long-term efficacy of the therapy fails a predefined efficacy threshold.

According to one example, a method for providing therapy to a patient via electrical stimulation is disclosed, the method comprising: determining, relative to a start time of providing the therapy, one or more efficacy times that correspond to an efficacy indicator; determining, according to the efficacy times, efficacy data items for the patient, the efficacy data items indicative of a response profile defined by one or more response variables; comparing the efficacy data items with the efficacy indicator; and generating, based on the comparison, a prediction of an expected response to the therapy manifesting in the patient at a prospective time.

According to another example, a system for providing therapy to a patient via electrical stimulation is disclosed, the system comprising: a memory configured to store an efficacy indicator including one or more efficacy times, the efficacy indicator corresponding to an electrical stimulation treatment for the patient; and one or more processors in communication with the memory, the one or more processors configured to: identify a set of stimulation parameters defining the electrical stimulation treatment; determine, based at least in part on the set of stimulation parameters, the one or more efficacy times that correspond to the efficacy indicator; determine efficacy data items for the patient, the efficacy data items indicative of a response profile defined by one or more response variables, wherein the response profile corresponds to the one or more efficacy times; compare the efficacy data items with the efficacy indicator; and generate, based on the comparison, an efficacy prediction of long-term efficacy of the electrical stimulation treatment as indicated by an extrapolation of the response profile over time.

According to another example, a non-transitory computer-readable storage medium having stored thereon instructions that, when executed, cause one or more processors to perform one or more of efficacy techniques is disclosed. For example, the non-transitory computer-readable storage medium having stored thereon instructions, that when executed, cause one or more processors to at least: identify a set of stimulation parameters defining an electrical stimulation treatment for a patient; determine, based at least in part on the set of stimulation parameters, one or more efficacy times that correspond to an efficacy indicator; determine, at the efficacy times, efficacy data items for the patient, the efficacy data items indicative of a response profile defined by one or more response variables; compare the efficacy data items with the efficacy indicator; and generate, based on the comparison, a prediction of the electrical stimulation treatment invoking an expected response in the patient over time relative to a start time of the electrical stimulation treatment.

The disclosure also provides means for performing any of the techniques described herein.

The summary is intended to provide an overview of the subject matter described in the disclosure. The summary is not intended to describe each illustrated example or every implementation of the disclosure nor is intended to provide an exclusive or exhaustive explanation of the systems, device, and methods described in detail within the accompanying drawings and description below. Further details of one or more examples of the disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1:
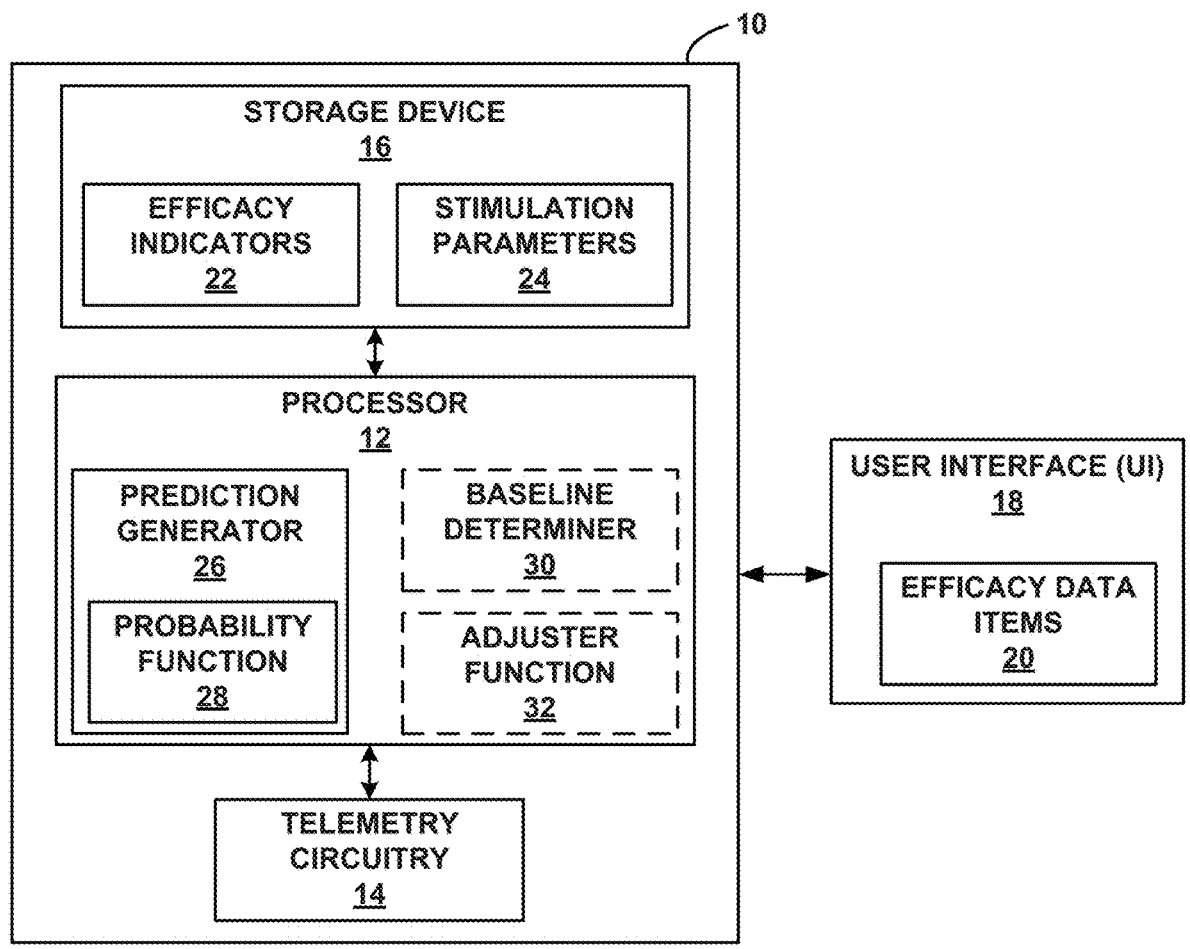
FIG. 1 is a functional block diagram illustrating an example computing device configured to perform one or more of the various techniques disclosed herein.

Systems, devices, and techniques for predicting the efficacy of an electrical stimulation treatment for a patient are described. A device configured to deliver electrical stimulation therapy, such as that of an implantable medical device (IMD), may provide electrical stimulation treatments to a patient pursuant to various therapy programs. In some instances, a healthcare professional (HCP) may determine an initial therapy program for a patient, such as during a trial period, and then may determine subsequent therapy programs for the patient in order to provide as much therapy for the patient as possible. In some examples, a therapy program may be configured to treat patients for pain, tremors, seizures, incontinence, and other ailments that a patient may treat with electrical stimulation therapy. In the case of electrical stimulation therapy, each therapy program may be defined by sets of stimulation parameters (e.g., amplitude, frequency, pulse width, electrode combinations, electrode polarities, lead locations, etc.) that may be iteratively adjusted over time, such as through various titration schemes. A device may adjust one or more stimulation parameters in order to optimize the therapy treatment and potentially achieve higher levels of efficacy with each adjustment to the therapy. In an example, a HCP may adjust parameters of the therapy programs over time based on how a patient responds to the therapy program as may be defined by one or more response variables. In another example, a computing device, such as an IMD programmer, may determine that a particular adjustment to the parameters would likely achieve an efficacious long-term response in the patient. The computing device may first receive confirmation from the HCP and/or patient before any changes to the therapy parameters are allowed.

In some examples, the computing device, such as the IMD programmer, a remote computing device (e.g., a server), or another computing device, may determine that a set of patients, when initially exposed to a therapy, are likely to experience fluctuating therapy efficacy over time in a way that the computing device may be modeled over time as an efficacy indicator. The efficacy indicator may take the form of a response model and/or historical response profiles that, in some examples, are correlated to particular stimulation characteristics and may be referenced based on an energy level of a stimulation therapy program used that produced particular response profiles in the past. In other words, fluctuations in efficacy may, under certain circumstances, manifest as a predictable efficacy indicator (e.g., a response profile), where efficacy markers in the fluctuations occur at identifiable efficacy times. Such efficacy times may be identifiable from the efficacy indicator. Accordingly, certain examples are directed toward correlating efficacy data items of a patient (e.g., measured response profiles of the patient) to a predicted efficacy indicator (e.g., predicted response profiles) to generate a prediction of long-term efficacy for the treatment (e.g., a therapy program).

When dealing with patient selection for spinal cord stimulation (SCS) therapy, it can be difficult to predict which are the best patients for specific therapy programs. A neuromodulation trial allows the patient to try different stimulation therapy programs for a certain period of time to assess the effectiveness of the treatment. In some examples, the effectiveness of the treatment may be measured by recorded pain relief values (e.g., pain scores). In such examples, recorded pain relief values, among other efficacy data items, may be stored in a storage device of the system as a set of response variables.

In various aspects of the disclosure, relevant parameters for the therapy programs can be grouped according to similarities between response profiles. A response profile generally refers to a collection of efficacy data items arranged chronologically so as to track changes in response variables over time. In an example, a response profile may include a first response variable indicating a positive response at a first time followed by a second response variable indicating a less positive response at a second time followed by a third response variable indicating a more positive response at a third time.

In one example, in the field of SCS, one group of therapy programs might be based upon a set of parameters for low frequency and low energy, such as combinations of 40-100 Hz, a pulse width (PW) of 180-450 microseconds (µs), 200-450 µs, and at amplitudes above sensory threshold. That is, low frequency SCS therapy may include a PW parameter of about 200-600 µs or in some instances, 180-450 µs or 200-450 µs. The low energy SCS therapy may be delivered at a first energy level that is defined by the therapy parameters of the SCS therapy.

In some examples, a characteristic of a therapy determined for patient 52 may include that the therapy involves a passive recharge pass, where a previous phase of the therapy may include a depolarizing phase at, for example, PWs between 200-600 µs. In such examples, the passive recharge characteristic may include an opposite polarity to that of the previous phase to allow stimulated tissue to return to a neutral charge.

In a non-limiting and illustrative example, another group of therapy programs might be based upon a set of parameters that is sometimes referred to as High Density (HD) stimulation. HD stimulation uses a higher frequency compared to that of the low frequency SCS therapy. In addition, HD stimulation delivers a high frequency SCS therapy with amplitudes below the sensory threshold. HD stimulation has sometimes been shown to be effective for patients that fail low energy or low frequency stimulation therapy. In some examples, HD stimulation further includes smaller PWs or the same PWs compared to that of the low frequency SCS therapy. An energy level (e.g., charge density) may be calculated generally based on the area under each pulse, which depends on the stimulation parameters (e.g., frequency, amplitude, pulse width, pulse shape, etc.). A first energy level may be achieved with a first set of parameters and a lower or higher energy level may be achieved with a second set of therapy parameters. In an example, parameters defining a low frequency SCS therapy may define a first energy level and parameters defining HD stimulation therapy may define a second energy level that is higher than the first energy level as determined from the various parameters of the respective stimulations. In addition, a first HD stimulation therapy may have a higher or lower energy level compared to a second HD stimulation therapy and a first low frequency stimulation therapy may have a lower or higher energy level compared to a second stimulation therapy, as measured from determining an integration metric that determines the effective area under a pulse or curve defined by the stimulation parameters, when the pulse or curve is represented graphically. In an illustrative example, a parameter combination of 40-100 Hz, a PW of 200-600 µs, and with an amplitude above sensory threshold may have a lower energy level (e.g., lower charge density) compared to higher frequency parameters used in, for example, an HD stimulation therapy.

In some examples, patients may exhibit a delay in a positive response or in some instances, a delay in exhibiting any response to HD stimulation, whether positive or negative. In an illustrative and non-limiting example, a patient may exhibit a two to three day delay into the stimulation period before exhibiting a positive response, such as an increase in pain relief or decrease in pain. This response may be tracked as a positive response variable that may be used to populate a developing response profile. In some instances, a negative response may follow the already delayed positive response, where, with the negative response, the patient may experience a temporary decrease in pain relief or an increase in how the patient rates any perceived pain (e.g., a negative response variable). The patient pain rating may factor into determining a pain score for the patient at any particular moment in time when the patient provides data regarding the efficacy of the treatment. Similar to the positive response, this negative response may be tracked as a negative response variable that may be used to populate the developing response profile. In addition, depending on the patient, stimulation parameters, or other therapy characteristics, the decrease in pain relief may be followed by another increase in pain relief at a third moment in time, where an efficacy of the treatment may again appear evident following the time when the treatment appeared ineffective. In any event, these types of delays in positive efficacy responses may lead to the patient being asked to continue the therapy for a minimum amount of time before determining whether the therapy program is effective and may also tend to lead to the manifestation of false negatives in the efficacy evaluation. In this illustrative example, the patient may be asked to continue the therapy for a minimum of three days before determining whether the therapy program is effective (and being able to try a different therapy program) and may also lead to false negatives. In one example, a patient that does not respond to HD stimulation soon after the start of stimulation (e.g., within 1 day) could be taken off from the HD stimulation without giving HD stimulation time to prove effective over a longer term, such as over a term of more than three days.

The aforementioned issues, among others, may be addressed by the disclosed efficacy prediction techniques by correlating measured response profiles to a predicted response profile to generate a prediction of long-term efficacy for the treatment. In some examples, an efficacy prediction may be based on comparison of a reliable indicator of response to HD parameters in the first hour of application of stimulation (e.g., a first efficacy time of an efficacy indicator) with an initial response to HD parameters (e.g., a first set of efficacy data items).

In an illustrative example, an initial response to HD parameters, such as a positive response, may manifest within the first 15 minutes of HD stimulation and then the response may subside thereafter for a relatively prolonged period of time in which the HD stimulation appears to have no effect when observed based only on the lack of response during the prolonged period of time. In this example, however, there may be a second phase of positive response starting 48-72 hours later (e.g., a second efficacy time). According to one or more techniques of the disclosure, a computing device may compare the short-term response to HD stimulation in patients with a particular efficacy indicator to generate a prediction that the patient will respond positively to HD parameters in the long-term (e.g., at a prospective time). In another example, the computing device may determine the efficacy indicator based on the stimulation parameters of the therapy (e.g., HD stimulation, lower charge density stimulation, etc.) and determine the one or more efficacy times from the efficacy indicator. The computing device may output the one or more efficacy times as an instruction for systematically collecting efficacy data items during the efficacy data times.

In some examples, the computing device, such as the IMD programmer, a remote computing device (e.g., a server), or another computing device, may generate a prediction of whether an initial or subsequent therapy program is likely to provide long-term efficacious results by first determining an efficacy indicator that specifically corresponds to a particular therapy program determined for the patient or an efficacy indicator that specifically corresponds to characteristics of the therapy program. The computing device may determine from the efficacy indicator a set of particular time intervals (e.g., efficacy times) relative to a starting time of the therapy that align with particular efficacy markers (e.g., peaks in positive responses to the therapy) of the efficacy indicator. If a particular time interval has passed, the computing device may determine the presence of a set of efficacy data items that coincide with the particular past time intervals as those efficacy data items are available.

In some examples, the computing device may allocate a higher reliability weight to efficacy data items that coincide with the determined efficacy times (e.g., a first set of data items at 45-minutes following a start of therapy, a second set of data items at an 80-hour mark following the start of the therapy, etc.). The computing device may determine, from an efficacy indicator, one or more efficacy times. The computing device may then output the efficacy times. In an example, the computing device may generate a report including a summary of the determined efficacy times.

In some examples, the efficacy times may pertain specifically to the electrical stimulation therapy determined for the patient. In addition, the computing device may be configured to allocate a higher reliability weight to efficacy data items collected during particular efficacy times compared to efficacy data items that do not coincide with the determined efficacy times. The computing device may output, via a user interface, a summary report of the efficacy times with an indication that the efficacy times represent times in which data will provide a greater degree of certainty for the prediction. As such, a user of the computing device may determine from the indication when to collect efficacy data from the patient following a start time of the electrical stimulation therapy.

In some instances, the efficacy times may indicate when an electrical stimulation treatment should begin for a patient, such as in cases where the computing device has determined efficacy times based on parameters for the electrical stimulation treatment but where the electrical stimulation treatment has not yet commenced. In an example, the efficacy times may coincide with times that a patient may be unavailable to provide responses (e.g., response variables) due to a schedule of the patient. In such instances, a start time of the electrical stimulation treatment may be delayed, such that the efficacy times align with the schedule of the patient.

Over time, the computing device may determine the presence of efficacy data items that coincide with the determined efficacy times. In some instances, the computing device may provide a prompt coincident to those indicated efficacy times, where the prompt is configured to initiate the collection of efficacy data items from a patient. The prompt may include a push notification to a device of the patient. In such examples, the patient may input response variables (e.g., pain levels), via a user interface, at the determined times so as to allow the computing device to collect efficacy data items pursuant to the determined efficacy times and generate an efficacy prediction based on the efficacy data items and the efficacy indicator that guided the collection of the efficacy data items. In some examples, an efficacy prediction may represent a degree to which a particular treatment is likely to provide a particular therapeutic effect (e.g., pain relief, altering behavior, etc.), such as a likelihood of long-term efficacy for the particular treatment.

The disclosed technology is applicable to a variety of applications. While described in connection with particular implementations and/or applications, the techniques of the disclosure are not so limited, and it will be understood that the disclosed technology may apply in other contexts or via other mechanisms that, for sake of brevity, are not explicitly described with reference to each or all examples of the disclosure. In addition, the disclosure includes discussion of various examples, aspects, and features. Unless otherwise stated, the various examples, aspects, and features are contemplated as being used together in different combinations. For ease of discussion and as a practical matter, each possible combination of features is not expressly recited. For example, the disclosure refers to aspects relating to medical devices containing or used in connection with correlating various waveform parameters (e.g., voltage, amperage, frequency (Hz), pulse width, wave shape, etc.). It is understood that there can be many different types of waveform parameters and combinations of multiple waveform parameters.

FIG. 1 is a block diagram of an example computing device 10, according to one or more of techniques of the disclosure. Computing device 10 may be configured to perform one or more of the various techniques of the disclosure. In an example, computing device 10 may determine the efficacy times and output the efficacy times to another device or in some examples, may generate a long-term efficacy prediction in accordance with one or more of the various techniques of the disclosure.

In some examples, computing device 10 may include one or more computing device(s) 10, such as one or more computing device(s) 10 implemented via a computing network. In an example, computing device 10 may be implemented via one or more computing device(s) 10 that execute various functions over a cloud computing network, edge computing network, neural network (e.g., artificial neural network, deep neural network, etc.), or various other computing networks or combinations of computing networks. As such, computing device(s) 10 may be referred to in some instances herein as a plurality of "computing device(s) 10," while in other instances may be referred to simply as "computing device 10" as appropriate. While computing device(s) 10 may generally be described as a hand-held device, in some examples, computing device(s) 10 may include a larger portable device or a more stationary device, such as a bedside monitor or workstation.

In some examples, computing device(s) 10 may include one or more of a cellular phone, a "smartphone," a satellite phone, a notebook computer, a tablet computer, a wearable device, a computer workstation, one or more servers, a personal digital assistant, a handheld computing device, virtual reality headsets, wireless access points, motion or presence sensor devices, or any other computing device that may run an application that enables the computing device to interact with one or more medical devices, such as an IMD, or in some instances, may interact with another computing device that is, in turn, configured to interact with one or more medical devices.

Computing device 10 comprises any suitable arrangement of hardware, alone or in combination with software and/or firmware, to perform the techniques attributed to computing device 10, including processor 12 and/or storage device 16. In various examples, processor 12 may include one or more processors, such as one or more microprocessors, digital signal processors (DSPs), application specific integrated circuits (ASICs), field programmable gate arrays (FPGAs), programmable logic circuitry, complex programmable logic devices (CPLDs), or any other equivalent integrated or discrete logic circuitry, or the like, either alone or in any suitable combination.

In some examples, particular computing device(s) 10 may include user interface (UI) 18 and/or telemetry circuitry 14. In such instances, UI 18 and/or telemetry circuitry 14 may be optionally included with computing device 10.

As described, computing device 10 may optionally include UI 18. In some examples, UI 18 may be a graphical UI (GUI), an interactive UI, etc. In some examples, UI 18 may further include a command line interface. In some examples, computing device 10 may include a display system (not shown). In such examples, the display system may comprise system software for generating UI data to be presented for display and/or interaction. In some examples, processing circuitry, such as that of processor 12, may receive UI data from another device that computing device 10 may use to generate UI data to be presented for display and/or interaction.

In some examples, UI 18 may include a display, which may, for example, be a liquid crystal display (LCD) or light-emitting diode (LED) display, or organic light-emitting diode (OLED). In some examples, a display of computing device 10 may include a touch screen display, and a user may interact with computing device 10 via the display. It should be noted that the user may also interact with computing device 10 remotely via a network computing device.

In some examples, UI 18 may include a keypad, which, in some examples, may include the keypad together with the display. The keypad may take the form of an alphanumeric keypad or a reduced set of keys associated with particular functions. Computing device(s) 10 may additionally or alternatively include a peripheral pointing device, such as a mouse, via which the user may interact with UI 18. In some instances, UI 18 may include a UI that utilizes virtual reality (VR), augmented reality (AR), or mixed reality (MR) UIs, such as those that may be implemented via a VR, AR, or MR headset. UI 18 may further include a softkeys, hard keys (e.g., physical buttons), lights, a speaker and microphone for voice commands.

UI 18 may be configured to display any information related to the delivery of stimulation therapy, such as currently selected parameter values, intensity level thresholds, or any other therapy information. Computing device 10 may also receive user input via UI 18, whether UI 18 is part of computing device 10 or not. The input may be, for example, in the form of pressing a button on a keypad or selecting an icon from a touch screen. The input may request starting or stopping electrical stimulation, or requesting some other change to the delivery of electrical stimulation.

In addition, computing device 10 may be configured to receive, via UI 18, input from the user, such as efficacy data items 20. The efficacy data items 20 may include information about how the patient is feeling about the treatment, such as their level of satisfaction with the treatment. The level of satisfaction may be determined by the level of pain the patient is feeling or by patient answers to questions such as whether the patient is feeling the treatment, whether the patient is feeling the treatment all the time, or just some of the time, and if they are uncomfortable. In addition, efficacy data items 20 may include pain scores. In an example, computing device 10 may determine a pain score for the patient based on user input, such as a pain score on a scale from no pain to extreme pain.

As illustrated in FIG. 1, each one of computing device(s) 10 include at least one processor 12 and at least one storage device 16. Processor 12 may be configured to perform one or more of the various techniques of the disclosure, e.g., via prediction generator 26, baseline determiner 30, and/or adjuster function 32. In some instances, baseline determiner 30 and/or adjuster function 32 may be optional to computing device 10. As described herein, prediction generator 26 may determine a probability function 28 that adjuster function 32 may reference in order to adjust (e.g., titrate) stimulation parameters 24. In some examples, prediction generator 26 may include an artificial intelligence (AI) engine and/or machine learning (ML) model that is trained on stimulation parameters, patient characteristics, response profile characteristics, etc. to determine an efficacy indicator and/or efficacy times that correspond to an efficacy indicator. In addition, prediction generator 26 may generate a long-term prediction based on efficacy data items 20 and efficacy indicators 22 that include efficacy time indications that correspond to efficacy data items 20. Prediction generator 26 may determine an efficacy time indication based on an efficacy marker of the efficacy indicator, such as a peak in a predicted response profile that exceeds a particular static or, in some instances, a dynamic threshold.

In some examples, various components described with reference to processor 12 of FIG. 1, including prediction generator 26, baseline determiner 30, and adjuster function 32, may be implemented as fixed-function circuitry or on programmable circuitry. In an example, prediction generator 26 may be implemented in circuitry as part of the processing circuitry of processor 12, where the processing circuitry is configured to perform one or more of the various prediction techniques described herein. In another example, adjuster function 32 may be implemented by processor 12 and telemetry circuitry 14, such that adjuster function 32 may adjust stimulation parameters 24 of a therapy program based on probability function 28.

In various examples, storage device 16 may include one or more various memory devices, such as random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), flash memory, comprising executable instructions for causing the one or more processors to perform the actions attributed to them. Moreover, although processor 12 and telemetry circuitry 14 are described as being separate, in some examples, processor 12 and telemetry circuitry 14 are functionally integrated. In some examples, processor 12 and telemetry circuitry 14 correspond to individual hardware units, such as ASICs, DSPs, FPGAs, or other hardware units.

Storage device 16 may store instructions that, when executed by processor 12, cause processor 12 and computing device 10 to provide the functionality ascribed to computing device 10 throughout the disclosure. In some examples, storage device 16 stores one or more therapy programs (e.g., stimulation parameters 24) for execution by an IMD to deliver electrical stimulation therapy. In some examples, the therapy programs, defined at least in part by stimulation parameters 24, correspond to electrical stimulation waveforms, such as waveforms employed for SCS, DBS, etc.

In some examples, storage device 16 may include efficacy indicators 22. In some instances, storage device 16 may store a particular efficacy indicator 22 that corresponds to a specific set of stimulation parameters 24. In another example, storage device 16 may include an efficacy indicator database, such as efficacy indicator database 50 described with reference to FIG. 2, where the database includes a wide array of efficacy indicators 22. In any case, processor 12 may determine efficacy indicator 22 based on the set of stimulation parameters 24 used for a particular electrical stimulation therapy. In an example, prediction generator 26 may identify characteristics of a particular therapy provided a patient, such as stimulation parameters 24, electrode combinations, implantation locations, electrode polarities, time since a start of the therapy, such as a time since an adjustment of a stimulation parameter, amount of adjustment to the stimulation parameters over time, such as a number of titrations, IMD type, whether the IMD represents a particular type of IMD, replacement IMD, etc. Processor 12, e.g., via prediction generator 26, may then query a database of efficacy indicators (e.g., predetermined response profiles), such as in efficacy indicators 22 stored in storage device 16 and/or efficacy indicator database 50, to determine an efficacy indicator that corresponds to the particular therapy of a patient. In such examples, processor 12 may determine, as an efficacy indicator, a predicted response profile based at least in part on stimulation parameters 24. Processor 12 may deploy a baseline determiner 30 (e.g., AI engine and/or ML model) to determine from efficacy indicator 22 a set of efficacy times that correspond to particular behaviors of efficacy indicator 22 (e.g., peak at first efficacy time, dip at second efficacy time, peak at third efficacy time). In such instances, processor 12 may output the set of efficacy times, or at least those efficacy times in which the response variables are expected to exhibit predicted behaviors (e.g., peak above a predefined threshold, change by a particular percentage amount, change by an amount proportional to a peak amount, etc.).

In some examples, processor 12 may determine a specific efficacy indicator 22 that corresponds to particular therapy characteristics. In an example, processor 12 may utilize the specific efficacy indicator 22 to perform an efficacy prediction. Efficacy indicator 22 may represent one or more efficacy times. In such examples, efficacy times of efficacy indicator 22 may represent times at which efficacy data items 20, alone or in the aggregate, are expected to be more indicative of a long-term efficacy of the therapy (e.g., stimulation parameters 24) compared to a prediction based on efficacy data items 20 corresponding to times that do not correspond to any one of the efficacy times. That is, efficacy data items 20 corresponding to intermediate times, taken alone or out of context with the efficacy data items 20 corresponding to the determined efficacy times, are less likely to indicate a true likelihood of long-term efficacy of the therapy for the patient.

In some examples, prediction generator 26 may determine efficacy indicator 22 anew, such as by deploying an artificial intelligence (AI) engine and/or a machine learning (ML) model trained to determine efficacy indicators 22 based on various sets of training data. That is, prediction generator 26 may deploy an AI engine and/or a ML model trained to determine efficacy indicators 22. The training data sets may include, for example, historical efficacy indicators, historical therapy characteristics, historical response variables, dispositions of a therapy as it pertains to particular patients, or combinations thereof.

In some examples, computing device 10 may determine one or more specific efficacy indicators 22 from storage device 16 based on a therapy program determined for a patient. In another example, computing device 10 may retrieve from an efficacy indicator database 50 (FIG. 2) that stores a plurality of efficacy indicators 22. Similar to storage device 16, efficacy indicator database 50 includes efficacy indicators 22 that relate to various therapy programs. In some examples, storage device 16 may acquire, in response to a database query, the one or more efficacy indicators 22.

In addition, baseline determiner 30 may determine a baseline threshold for a given efficacy indicator 22 that defines an efficacy baseline (e.g., a withdrawal threshold) that may be the same or different for multiple efficacy times of efficacy indicator 22. In an example baseline determiner 30 may determine a lower efficacy baseline threshold for a first efficacy time of efficacy indicator 22 and a higher efficacy baseline threshold for a second efficacy time of efficacy indicator 22. In another example, baseline determiner 30 may determine a common efficacy baseline for all efficacy times of efficacy indicator 22. Predication generator 26 may determine whether efficacy data items 20 collected during each of the efficacy times satisfy the one or more efficacy baseline thresholds. In some examples, prediction generator 26 may predict a high likelihood of long-term efficacy where a series of comparisons at different efficacy times indicate the plurality of efficacy data items 20 satisfying a baseline threshold or each individual baseline threshold that corresponds with each of the different efficacy times.

In some example, efficacy indicator 22 may represent one or more response profiles that span at least a predefined period of time (e.g., long-term response profiles). Such efficacy indicators may represent one or more sub indicators (e.g., peaks in pain relief at particular efficacy times, prolonged peaks, etc.) that span various times of at least the predefined period of time (e.g., 1 week, 1 year, etc.) of the one or more response profiles. Sub indicators may include peaks in pain relief at particular times relative to a start of a therapy program or following adjustment of a therapy program.

In one example, prediction generator 26 may determine efficacy indicator 22 based on an analysis of common trends between a mass of historical response profiles. In some instances, prediction generator 26 may be implemented by a network server that includes processing circuitry coupled to memory that stores efficacy indicators 22 and/or stimulation parameters 24, such as storage device 16. Processor 12 may extract and manipulate the common trends based on a context that results in each response profile (e.g., patient information, IMD information, therapy characteristics, etc.). Processor 12 may then determine a set of efficacy times for efficacy indicator 22 and store the set of efficacy times with the efficacy indicator 22.

In some examples, processor 12 may store the efficacy times in a look-up table (LUT). In such examples, the LUT may relate efficacy indicators 22 to efficacy times, such as relating a first efficacy indicator 22 to a first set of determined efficacy times, a second efficacy indicator 22 to a second set of determined efficacy times, etc. In another example, processor 12 may store the efficacy times as metadata for a particular file that defines a particular efficacy indicator 22. As such, processor 12 may determine particular efficacy times to assign efficacy indicator 22 as part of the metadata of efficacy indicator 22. In an illustrative example, processor 12 may determine an efficacy indicator 22 that corresponds to a particular therapy program, such as based on patient biomarkers, stimulation parameters, energy level of the therapy, patient cohort data, or other therapy characteristics. As such, processor 12 may access as part of efficacy indicators 22 a LUT that indicates one or more efficacy times that correspond to the particular efficacy indicator 22. The LUT may further define baseline thresholds that are expected at the efficacy times or may define a single baseline threshold for a determined efficacy indicator 22.

Figure 2:
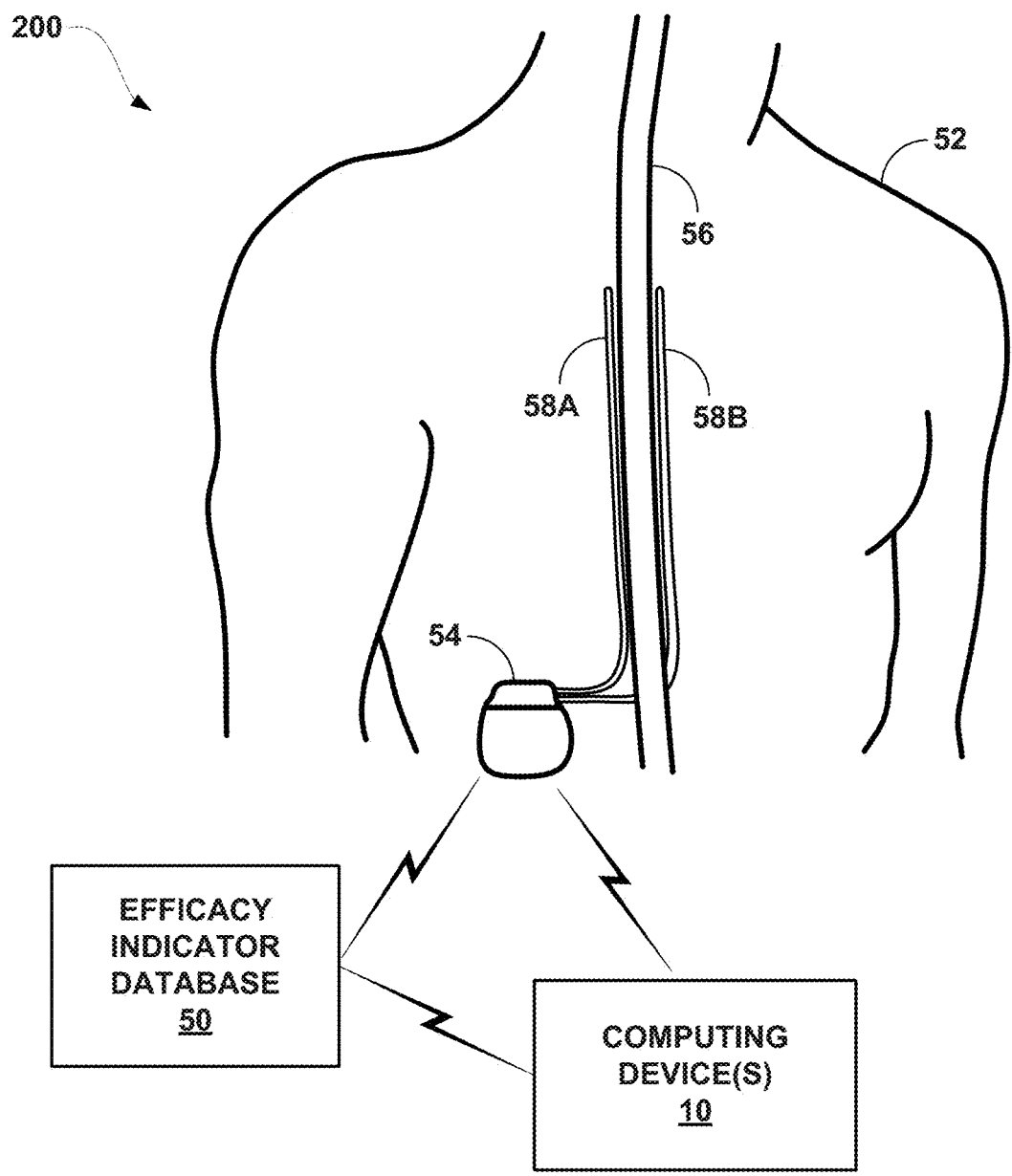
FIG. 2 illustrates an example environment of the computing device of FIG. 1 in conjunction with an example spinal cord stimulation (SCS) system, in accordance with one or more of the various techniques disclosed herein.

In some examples, processor 12 may determine a particular efficacy indicator 22 and determine efficacy times that correspond to the particular efficacy indicator 22. In such examples, processor 12 may determine a particular efficacy indicator 22 that is specific to a particular therapy context of patient 52 (FIG. 2). As described herein, the efficacy times determined from the particular efficacy indicator 22 indicate whether efficacy data items 20 received via processor 12 coincide with the one or more efficacy times defined by efficacy indicator 22. With alignment of the obtained efficacy data items 20 and the determined efficacy times, processor 12 may effectively compare the obtained efficacy data items 20 to efficacy indicator 22. That is, processor 12 may determine that the obtained efficacy data items 20 are in alignment with the determined efficacy times where the efficacy data items 20 includes timestamps that coincide with the efficacy times.

In some instances, processor 12 may determine, from an efficacy indicator 22, an efficacy time that includes a predefined time margin. In such examples, efficacy indicator 22 may define the time margin. In an illustrative example, a first efficacy indicator 22 may indicate a first efficacy time of 6 hours and a time margin that includes, for example, 10 minutes prior to the first efficacy time, and 20 minutes after the first efficacy time. That is, if the therapy began at 3:00 pm, the first efficacy time may be 9:00 pm where a peak in pain relief is expected to occur that exceeds a particular threshold. The first efficacy indicator 22 may define the threshold that indicates a particular value of pain relief that is expected to occur during the first efficacy time. In such examples, processor 12 may obtain efficacy data items 20 (e.g., pain scores, physiological parameters, etc.) during the first efficacy time (e.g., 8:50 pm to 9:20 pm). Processor 12 may obtain efficacy data items 20 from a wearable device or via UI 18. Processor 12 may determine that the efficacy data items 20 align with the first efficacy time.

In some examples, processor 12 may determine that a comparison of efficacy data items 20 obtained during the first efficacy time may be compared to portions of efficacy indicator 22 that correspond to the first efficacy time. Portions of a particular efficacy indicator 22 may include historical response variables, known positive responders (e.g., peaks that exceed a particular variable value for a prolonged period of time), etc. Based on the comparison, processor 12 may generate a prediction as to whether the therapy is likely to provide long-term efficacy.

In an example, processor 12 may compare the obtained efficacy data items 20 to determine a likelihood of long-term efficacy for the patient. Efficacy indicator 22 may be based on a collection of historical response profiles that integrate responses from models or actual patients over time in order to model a predicted (e.g., expected) response profile pursuant to a particular therapy.

A trained ML model and/or AI engine may be configured to process and analyze the user input (e.g., efficacy data items 20), efficacy indicators 22 (e.g., predicted response profiles, efficacy times of the predicted response profiles), and/or physiological parameters, in accordance with certain examples of the disclosure where ML models or AI engines are considered advantageous (e.g., predictive modeling, inference detection, contextual matching, etc.). Examples of ML models and/or AI engines that may be so configured to perform aspects of the disclosure include classifiers and non-classification ML models, artificial neural networks (NNs), linear regression models, logistic regression models, decision trees, support vector machines (SVM), Naïve or a non-Naïve Bayes network, k-nearest neighbors (KNN) models, deep learning (DL) models, k-means models, clustering models, random forest models, or any combination thereof. Depending on the implementation, the ML models may be supervised, unsupervised or in some instances, a hybrid combination (e.g., semi-supervised).

In an example, prediction generator 26 may collect efficacy data items 20 at particular efficacy times (e.g., predetermined time points). As described herein, the efficacy times may be defined by one or more of the selected efficacy indicators 22 (e.g., one efficacy indicator 22 or a combination of efficacy indicators 22). Prediction generator 26 may train a ML model and/or AI engine on efficacy data items 20 collected at the determined efficacy times. As such, prediction generator 26 may retrospectively analyze efficacy data items 20 and adjust parameters of the ML model and/or AI engine to learn to make more accurate predictions of long-term efficacy for future iterations.

In some examples, prediction generator 26, baseline determiner 30, and/or adjuster function 32 may include trained ML model(s) and/or AI engine(s). In an example, processor 12 may train baseline determiner 30 on historical efficacy data items 20 and corresponding treatment information to determine a plurality of efficacy indicators 22. Processor 12 may store the determined efficacy indicators 22 as baseline response profiles and may then populate an efficacy indicator database 50 (FIG. 2). In another example, processing circuitry of a separate device, such as a remote data server, may deploy trained ML model(s) and/or AI engine(s) to determine efficacy indicators 22 for subsequent retrieval via efficacy indicator database 50. That is, processing circuitry of the remote data server, similar to that of processor 12, may determine specific efficacy indicators 22 for various therapy characteristics, such as for each type of treatment and/or a patient cohort, and may store the determined efficacy indicators 22 to efficacy indicator database 50.

In an illustrative example, processor 12 may determine a specific efficacy indicator 22 for each treatment and/or a patient cohort to model how particular subjects, such as patient 52 of FIG. 2, have responded to treatments over time. Prediction generator 26 may then determine, as efficacy times, times in which initial responses or particular responses may likely manifest in a particular type of patient receiving a particular therapy. As such, prediction generator 26 may determine efficacy times to store as an efficacy indicator 22 or to store efficacy times along with an efficacy indicator 22 (e.g., as metadata for the efficacy indicator 22). In another example, these models and/or engines may be trained to determine, from a plurality of efficacy indicators 22, efficacy markers within the efficacy indicators 22, such as peaks in positive response variables, particular changes in response variables indicative of a potential worsening condition at a prospective point in time. In addition, these models and/or engines may isolate efficacy times (e.g., time segments, windows, etc.) from efficacy indicators 22.

In some examples, computing device 10 may include telemetry circuitry 14. Telemetry circuitry 14 may support wireless communication between IMD 54, described with reference to FIG. 2, and computing device 10 under the control of processor 12. Telemetry circuitry 14 may also be configured to communicate with another computing device via wireless communication techniques, or direct communication through a wired connection. In some examples, telemetry circuitry 14 may provide wireless communication via an RF or proximal inductive medium. In some examples, telemetry circuitry 14 may include an antenna, which may take on a variety of forms, such as an internal or external antenna.

Examples of local wireless communication techniques that may be employed to facilitate communication between computing device 10 and IMD 54 include RF communication according to the 802.11 or Bluetooth® specification sets or other standard or proprietary telemetry protocols. In this manner, other external devices may be capable of communicating with computing device(s) 10 without needing to establish a secure wireless connection.

In some examples, computing device 10 may include a non-user device, such as a remote server, that outputs data (e.g., efficacy times) to a user device that may be another one of computing device(s) 10. In some examples, UI 18 may receive user input, such as efficacy data items 20. A computing device 10 that includes UI 18 may then store efficacy data items 20 in storage device 16. In another example, computing device 10 may transmit efficacy data items 20 to another one of computing device(s) 10, where computing device 10 may store efficacy data items 20 to storage device 16. In an illustrative example, computing device 10 may include a data server that receives efficacy data items 20, determines efficacy data items 20 that comply with the efficacy times specified by efficacy indicator 22, and stores each in storage device 16, prior to generating a prediction of long-term efficacy via prediction generator 26.

In some examples, computing device 10 may be an IMD programmer configured to provide control input to an IMD to deliver electrical stimulation pursuant to stimulation parameters 24. In such examples, computing device 10 may determine, relative to a start time of providing the electrical stimulation, one or more efficacy times that correspond to efficacy indicator 22. Computing device 10 may output the one or more efficacy times, via UI 18, as an indication to schedule check-in responses at particular time intervals that align with the efficacy times. In addition, computing device 10 may determine, according to the efficacy times, efficacy data items 20 for the patient, where efficacy data items 20 are indicative of a response profile of that patient that has been defined by one or more response variables. Computing device 10 may then compare efficacy data items 20 to efficacy indicator 22. In an example, computing device 10 may compare, to efficacy indicator 22, efficacy data items 20 that correspond to the efficacy times and may in some instances, set aside efficacy data items 20 that may not correspond to the efficacy times. In any case, computing device 10 may generate, based on the comparison, a prediction of long-term efficacy of the electrical stimulation.

In some examples, computing device 10 may identify, via processor 12, a set of stimulation parameters defining the electrical stimulation treatment. Computing device 10 may then determine, based at least in part on the set of stimulation parameters, the one or more efficacy times that correspond to the efficacy indicator. Computing device 10 may additionally determine efficacy data items 20 for the patient. In such examples, the efficacy data items 20 are indicative of a response profile defined by one or more response variables.

Response variables may include input received from a patient. In an example, response variables may include answers a patient provides to a survey regarding pain relief the patient is experiencing (e.g., pain scores). The response variables may further include efficacy data received from a measurement device. In an example, a measurement device, such as an automated measurement apparatus, von Frey apparatus, etc., may be configured to elicit a response from patient 52 Computing device 10 may interface with the measurement apparatus via telemetry circuitry 14 and store the response variables as part of efficacy data items 20. The measurement apparatus in some instances may be a device worn by the patient that is configured to determine efficacy data in accordance with the determined efficacy times, such as by performing an efficacy measurement during particular efficacy times. Examples of response variables include one or more pain scores, paresthesia sensation levels, behavioral changes, etc. In an example, processor 12 may determine a pain score by determining a pain relief level indicated by the patient and biasing the pain relief level to determine the pain score. In general, response variables refer to a quantifiable response from patient in response to the therapy, such as a particular level of pain relief perceived by the patient or other sensation perceived by the patient.

In some examples, computing device 10 may receive efficacy data items 20 from another device, such as a device that includes UI 18 where computing device 10 may not include UI 18 in some instances. Computing device 10 may then compare the efficacy data items 20 to corresponding data items of efficacy indicator 22 or to one or more baseline thresholds defined by efficacy indicator 22. Based on the comparison, computing device 10 may generate a prediction of the long-term efficacy of the electrical stimulation therapy. In an example, computing device 10 may compare efficacy data items 20 that have been determined at a first efficacy time defined by efficacy indicator 22 to a baseline threshold that corresponds to the first efficacy time. In some examples, prediction generator 26 may determine efficacy data items 20 that correspond to a first efficacy time defined by efficacy indicator 22. Efficacy indicator 22 may further be defined by a plurality of historical efficacy data items or efficacy data items based on historical data. In such examples, prediction generator 26 may compare input efficacy data items 20 that correspond to the first efficacy time to corresponding efficacy data items that define the efficacy indicator 22 to determine whether the input efficacy data items 20 align with the corresponding efficacy data items of efficacy indicator 22.

In some examples, prediction generator 26 may compare efficacy data items 20 to various baseline thresholds defined by efficacy indicator 22 to determine a pattern in response profiles for particular patients receiving a particular type of therapy. In such examples, prediction generator 26 may be trained to identify patterns based on an analysis of historical response profiles. When determining a particular efficacy indicator 22, prediction generator 26 may determine a set of historical response variables that represent common values at a particular times across multiple efficacy indicators 22 (e.g., historical long-term response profiles). In some examples, prediction generator 26 may designate such times as efficacy times that correspond to the efficacy indicator 22. In some examples, a set of historical response variables that satisfy certain criteria (e.g., peak above a baseline threshold for greater than an expected period of time) indicate a higher likelihood of long-term efficacy for some patients and indicate a lower likelihood of long-term efficacy for other types of patients. Prediction generator 26 may determine an efficacy indicator 22 that includes efficacy times. The efficacy times may include as part of efficacy indicator 22 weighting values in which prediction generator 26 is configured to assign particular prediction weights to data items corresponding to particular efficacy times and assign more or less prediction weight to data items corresponding to other efficacy times or data items that do not correspond to any identified efficacy time.

In an illustrative example, a patient may provide, via patient feedback, indications as to the perceived efficacy of the current treatment. The patient feedback includes efficacy data items 20 that, when modeled over time, represent a short-term response profile of the patient. As described, the short-term response profile may span a timeframe relative to a start time of the treatment. The techniques of the disclosure involve utilizing the efficacy indicator 22 (e.g., a predetermined response profile) to determine a probability that the therapy program will provide a particular positive result for at least a predefined period of time, such as to determine the probability of long-term efficacy, or a likelihood for long-term efficacy manifesting at a particular prospective time, such as at a future point in time. The predicted time of long-term efficacy may include a time period defined by the efficacy indicator 22, or in some instances, may include an even longer period of time that extends beyond that of a timeframe defined by efficacy indicator 22.

In some examples, the techniques of the disclosure relate to the use of electrical stimulation wave forms applied to the spinal cord to reduce pain. While not necessarily limited to such applications, various aspects of the disclosed technology may be appreciated through a discussion of various examples using this context.

FIG. 2 illustrates an example environment for implementation of computing device 10 of FIG. 1 in conjunction with an example spinal cord stimulation (SCS) system 200. As shown in FIG. 2, system 200 includes an IMD 54, leads 58A, 58B, and computing device(s) 10 (e.g., one or more external computing device(s) 10), shown in conjunction with a patient 52. Patient 52 is ordinarily, but not necessarily, a human patient.

Although FIG. 2 is described with reference to SCS therapy, e.g., used to treat pain, the techniques of the disclosure are not so limited, and persons skilled in the art will understand that the techniques of the disclosure may be implemented in other contexts (e.g., neurological, orthopedic, etc.). SCS is described with reference to FIG. 2 to illustrate example implementations of various efficacy prediction and/or parameter adjustment techniques of the disclosure in order to provide an example environment or context in which the techniques may be applied. In some examples, however, system 200 may be configured to treat any other condition that may benefit from electrical stimulation therapy. In some examples, system 200 may be used to treat tremors, Parkinson's disease, epilepsy or sexual dysfunction), obesity, gastroparesis, or psychiatric disorders (e.g., depression, mania, obsessive compulsive disorder, anxiety disorders, and the like). In this manner, system 200 may be configured to provide therapy taking the form of deep brain stimulation (DBS), pelvic stimulation, peripheral nerve stimulation (PNS), peripheral nerve field stimulation (PNFS), cortical stimulation (CS), gastrointestinal stimulation, muscle stimulation or any other stimulation therapy capable of treating a condition of patient 52. That is, in some examples, IMD 54 may be an IMD configured to perform one or more of a variety of different stimulation therapies. In another example, IMD 54 may be an IMD configured to operate as a pacemaker, a cardioverter, and/or defibrillator, or otherwise monitor the electrical activity of the heart of patient 4 and provide pacing pulses to the heart of patient 4 based on the electrical signals sensed within the heart of patient 4.

In the example of FIG. 2, IMD 54 is an implantable electrical stimulator that is configured to generate and deliver electrical stimulation therapy to patient 52 via electrodes of leads 58A, 58B, e.g., for relief of chronic pain or other symptoms. In some examples, one of or both of the electrodes of leads 58A and 58B may be placed below the T9-10 spinal disc space and/or within 2 mm of spinal cord 56 for power efficient pain relief. IMD 54 may be a chronic electrical stimulator that remains implanted within patient 52 for weeks, months, or even years. In other examples, IMD 54 may be a temporary (e.g., trial) stimulator used to screen or evaluate the efficacy of electrical stimulation for chronic therapy (e.g., long-term therapy). In either instance, the techniques of the disclosure may generate an efficacy prediction as to the efficacy of the electrical stimulation for chronic therapy based on actual responses to stimuli elicited from patient 52 or from a medical device of patient 52 (e.g., a wearable device) at particular times compared against one of efficacy indicators 22, such as one of efficacy indicators 22 obtained from efficacy indicator database 50 based on treatment information pertaining to IMD 54 and/or patient 52. Such treatment information may include a type of IMD 54 used to deliver electrical stimulation, a set of stimulation parameters 24 used to deliver electrical stimulation (e.g., particular therapy programs 70, HD parameter settings, etc.), biomarkers of patient 52, an implant location (e.g., proximity to particular spinal discs type of therapy, region of brain, etc.), or other information as such that corresponds to particular treatments of a particular patient 52.

Electrical stimulation energy, which may be constant current or constant voltage based pulses (each pulse having relatively the same current or voltage), for example, is delivered from IMD 54 to one or more target tissue sites of patient 52 via one or more electrodes (not shown) of implantable leads 58A and 58B (collectively, "leads 58"). In the example of FIG. 2, leads 58 carry electrodes that are placed adjacent to the target tissue of spinal cord 56. One or more of the electrodes may be disposed at distal tips of leads 58 and/or at other positions, such as at intermediate points along the leads. Leads 58 may be implanted and coupled to IMD 54. The electrodes may transfer electrical stimulation generated by an electrical stimulation generator of IMD 54 to tissue of patient 52. Although leads 58 may each be a single lead, leads 58 may include a lead extension or other segments that may aid in implantation or positioning of leads 58. In one non-limiting and illustrative example, leads 58 may include an octopolar lead implanted in the epidural space of patient 52, such as proximate the lumbar level of spinal cord 56.

In some examples, IMD 54 may be a leadless stimulator with one or more arrays of electrodes arranged on a housing of the stimulator rather than leads that extend from the housing. In addition, in some other examples, system 200 may include one lead or more than two leads, each coupled to IMD 54 and directed to similar or different target tissue sites. The electrodes of leads 58 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy. The deployment of electrodes via leads 58 is described for purposes of illustration, but arrays of electrodes may be deployed in different ways.

The therapy parameters (also referred to herein as a set of electrical stimulation parameter values) for a therapy program that controls delivery of stimulation therapy by IMD 54 through the electrodes of leads 58 may include information identifying which electrodes have been selected for delivery of stimulation according to stimulation characteristics (e.g., the electrode configuration for the stimulation program, and voltage or current amplitude, pulse rate, and PW of stimulation delivered by the electrodes). In some examples, stimulation may be delivered in forms such as continuous waveforms. Other programs that control delivery of other therapies by IMD 54 may include other parameters, e.g., such as rate or the like in the case IMD 54 is also configured for drug delivery.

In some examples, leads 58 may include one or more sensors configured to allow IMD 54 to monitor one or more parameters of patient 52. The one or more sensors may be provided in addition to, or in place of, therapy delivery by leads 58. IMD 54 may be constructed of any polymer, metal, or composite material sufficient to house the components of IMD 54 (e.g., components illustrated in FIG. 3) within patient 52.

IMD 54 is configured to deliver electrical stimulation therapy (e.g., high dose, but not limited to high dose electrical stimulation therapy) to patient 52 via selected combinations of electrodes carried by one or both of leads 58, alone or in combination with an electrode carried by or defined by an outer housing of IMD 54. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 2, the target tissue is tissue proximate spinal cord 56, such as within an intrathecal space or epidural space of spinal cord 56, or, in some examples, adjacent to nerves that branch off of spinal cord 56. Leads 58 may be introduced into spinal cord 56 in via any suitable region, such as the thoracic, cervical or lumbar regions. In some examples, the electrodes of leads 58 may be introduced within 2 mm of the midline of the spine in an anterior/posterior or posterior/anterior view and/or below the T9-10 spinal disc space in a lateral view. Stimulation of spinal cord 56 may, for example, prevent pain signals from traveling through spinal cord 56 and to the brain of patient 52. Patient 52 may perceive the interruption of pain signals as a reduction in pain and, therefore, efficacious therapy results (e.g., a positive response).

IMD 54 generates and delivers electrical stimulation therapy to a target stimulation site within patient 52 via the electrodes of leads 58 to patient 52 according to one or more therapy programs. A therapy program defines values for one or more parameters 24 that define an aspect of the therapy delivered by IMD 54 according to that program. For example, a therapy program that controls delivery of stimulation by IMD 54 in the form of pulses may define values for voltage or current pulse amplitude, PW, and pulse rate (frequency) for stimulation pulses delivered by IMD 54 according to that program.

Moreover, in some examples, IMD 54 delivers electrical stimulation therapy to patient 52 according to multiple therapy programs, which may be stored as a therapy program group. In some examples, IMD 54 may deliver various pulses via respective electrode combinations. In addition, each electrode combination may correspond to a respective therapy program. In any case, the therapy programs may be stored as a group, such that IMD 54 may generate and deliver electrical stimulation therapy according to two or more therapy programs of a selected group. Each therapy program may correspond to an energy level that effectively identifies a class of efficacy indicators 22 for the therapy program. A particular efficacy indicator 22 may be determined from the class based on more specific items regarding the stimulation, such as a patient biomarker.

In some examples, processing circuitry 12 may determine an energy level of a particular therapy determined for patient 52. Processing circuitry 12 may then determine, based on the energy level, a class of efficacy indicators 22. In some examples, processing circuitry 12 may retrieve a class of efficacy indicators 22 from efficacy indicator database 50 that stores a plurality of efficacy indicators 22 for a plurality of different classes. In such examples, efficacy indicator database 50 or storage device 16 may classify the efficacy indicators 22 based on energy levels. Once processing circuitry 12 determines a class of efficacy indicators 22, processing circuitry 12 may determine a particular efficacy indicator 22 or multiple efficacy indicators 22 from the class of efficacy indicators 22 that correspond to the particular patient. In an example, processing circuitry 12 may determine efficacy indicator 22 based on particular factors in which efficacy indicators 22 tend to differ in various ways. In a non-limiting example, processing circuitry 12 may determine efficacy indicator 22 from the class of efficacy indicators 22 based on one or more biomarkers of patient 52. In an example, processing circuitry 12 may receive, via telemetry circuitry 14, indications of one or more patient biomarkers from IMD 54. Processing circuitry 12 may determine a particular efficacy indicator 22 based on one or more patient biomarkers that correspond to specific efficacy indicators 22 of a class that corresponds to other specific therapy characteristics, such as stimulation parameters 24. Computing device 10 may receive stimulation parameters 24 from IMD 54 via telemetry circuitry 66. IMD 54 may store the stimulation parameters as part of therapy programs 70.

In some examples, IMD 54 is configured to deliver a recharge signal (e.g., one or more recharge pulses or other waveforms), which may help balance a charge accumulation that may occur within tissue proximate the electrodes used to deliver the electrical stimulation. The recharge signal may also be referred to as a "recovery signal" or a "charge balancing signal" and may have a polarity opposite to that of the electrical stimulation signal generated and delivered by IMD 54. While recharge pulses are primarily referred to herein, in other examples, a recharge signal can have any suitable waveform.

In some examples, IMD 54 is configured to generate and deliver sub-threshold electrical stimulation therapy to patient 52 (e.g., via two or more electrodes). The amplitude, PW and/or frequency of the electrical stimulation signal may be selected such that a stimulation intensity level of the electrical stimulation signal is significantly less than an intensity level threshold for patient 52. In some examples, an intensity level threshold may include one or more of a perception threshold (e.g., an intensity-level perception threshold) or a paresthesia threshold (e.g., an intensity-level paresthesia threshold). A perception threshold generally refers to the lowest determined stimulation intensity level at which patient 52 perceives the electrical stimulation. A paresthesia threshold generally refers to the lowest determined stimulation intensity level at which the electrical stimulation causes paresthesia in patient 52. In some examples, paresthesia may occur with or without patient 52 perceiving the electrical stimulation, in which case the paresthesia threshold may be distinct from the perception threshold. In any case, patient 52 may provide such input to indicate whether various threshold have been satisfied via UI 18, such that computing device 10 may receive efficacy data items 20 (e.g., intensity levels, etc.).

In some examples, IMD 54 delivers stimulation signals with an intensity of 80% or less of the intensity level threshold of patient 52. In other examples, IMD 54 delivers stimulation signals with an intensity of 60% or less of the intensity level threshold of patient 52. In other examples, IMD 54 delivers stimulation signals with an intensity of 40% or less of the intensity level threshold of patient 52. In other examples, IMD 54 delivers stimulation signals with an intensity of 20% or less than the intensity level threshold of patient 52.

In some examples, IMD 54 delivers stimulation signals with an intensity in the range of 10% to 80% of the intensity level threshold of patient 52. In some examples, IMD 54 delivers stimulation signals with an intensity in the range of 20% to 80% of the intensity level threshold of patient 52. In some examples, IMD 54 delivers stimulation signals with an intensity in the range of 20% to 60% of the intensity level threshold of patient 52. In some examples, IMD 54 delivers stimulation signals with an intensity in the range of 40% to 60% of the intensity level threshold of patient 52. In some examples, IMD 54 delivers stimulation signals with an intensity in the range of 20% to 40% of the intensity level threshold of patient 52. In some examples, IMD 54 delivers stimulation signals with an intensity of approximately 20% of the intensity level threshold of patient 52. In one example, the stimulation signal has a PW of about 90 μs and frequency of about 1000 Hz.

In some examples, IMD 54 delivers the pulses of the sub-threshold electrical stimulation signal via different electrode combinations. For example, IMD 54 may alternate delivery of pulses between two different electrode combinations, or may otherwise interleave the pulses using two or more electrode combinations in any suitable order, regardless of the number of electrode combinations with which IMD 54 delivers the pulses.

A user, such as a clinician or patient 52, may interact with UI 18 of one or more of computing device(s) 10 to program IMD 54. Programming of IMD 54 may refer generally to the generation and transfer of commands, programs, or other information to control the operation of IMD 54. In this manner, IMD 54 may receive the transferred commands and programs from computing device 10 to control stimulation therapy. For example, computing device 10 may transmit therapy programs, stimulation parameter adjustments, therapy program selections, therapy program group selections, user input, or other information to control the operation of IMD 54, e.g., by wireless telemetry or wired connection.

In some cases, computing device 10 may be characterized as a physician or clinician programmer if it is primarily intended for use by a physician or clinician. In other cases, computing device 10 may be characterized as a patient programmer if it is primarily intended for use by patient 52. A patient programmer may be generally accessible to patient 52 and, in many cases, may be a portable device that may accompany patient 52 throughout the daily routine of patient 52. For example, a patient programmer may receive input from patient 52 when patient 52 wishes to terminate, change or provide information relating to the stimulation therapy. For example, patient 52 may provide information regarding the level of pain they are feeling or regarding their level of satisfaction with the stimulation therapy. In general, a physician or clinician programmer may support selection and generation of programs by a physician or clinician for use by IMD 54, whereas a patient programmer may support adjustment and selection of such programs by patient 52 during ordinary use.

As described herein, information may be transmitted between computing device(s) 10 and IMD 54. Therefore, IMD 54 and computing device(s) 10 may communicate via wireless communication using any techniques known in the art. Examples of communication techniques may include, for example, radiofrequency (RF) telemetry and inductive coupling, but other techniques are also contemplated. In some examples, computing device(s) 10 may include a communication head that may be placed proximate to a body of patient 52 near the IMD 54 implant site in order to improve the quality or security of communication between IMD 54 and computing device(s) 10.

Although IMD 54 is generally described herein, techniques of the disclosure may be applicable to external or partially external medical devices, as well. For example, IMD 54 may be configured as an external medical device coupled to one or more percutaneous medical leads. The external medical device may be a chronic, temporary, or trial electrical stimulator. In addition, an external electrical stimulator may be used in addition to one or more IMDs 54 to deliver electrical stimulation described herein.

In some examples, IMD 54 may be configured to deliver electrical stimulation therapy with electrical stimulation signals having sub-threshold (e.g., sub-paresthesia or sub-perception) intensity. For instance, patient 52 may not perceive the electrical stimulation (e.g., no paresthesia) but would experience therapeutic effect. The intensity of the electrical stimulation signal may be substantially lower than the intensity of the electrical stimulation signal at the intensity level threshold of patient 52.

As one example, the intensity of the sub-threshold electrical stimulation signal may be 80% or less of the intensity of the intensity level threshold of patient 52. As another example, the intensity of the sub-threshold electrical stimulation signal may be 60% or less of the intensity of the intensity level threshold of patient 52. As another example, the intensity of the sub-threshold electrical stimulation signal may be 40% or less of the intensity of the intensity level threshold of patient 52. As another example, the intensity of the sub-threshold electrical stimulation signal may be 20% or less of the intensity of the intensity level threshold of patient 52.

In some examples, IMD 54 delivers stimulation signals with an intensity in the range of 10% to 80% of the intensity level threshold of patient 52. In some examples, IMD 54 delivers stimulation signals with an intensity in the range of 20% to 80% of the intensity level threshold of patient 52. In some examples, IMD 54 delivers stimulation signals with an intensity in the range of 20% to 60% of the intensity level threshold of patient 52. In some examples, IMD 54 delivers stimulation signals with an intensity in the range of 40% to 60% of the intensity level threshold of patient 52. In some examples, IMD 54 delivers stimulation signals with an intensity in the range of 20% to 40% of the intensity level threshold of patient 52.

There may be a variety of waveforms of the sub-threshold electrical stimulation signals. As one example, the PW of the sub-threshold electrical stimulation signal may be 90 µs and the frequency may be 1000 Hz. The amplitude may be 20% of the amplitude at which patient 52 perceived the stimulation or experienced paresthesia. For instance, IMD 54 (e.g., automatically or in response to instructions from the clinician or patient 52) may start with stimulation having 90 µs PW and frequency of 1000 Hz, and titrate the amplitude upwards until patient 52 perceives the stimulation (e.g., arrives at the perception amplitude). As used herein, titration may involve either or both of: 1) changing the intensity (e.g., amplitude) of an electrical stimulation signal in a continuous manner such that stimulation is delivered to patient 52 during titration as the electrical stimulation signal is "ramped-up" or "ramped-down"; or 2) changing the intensity (e.g., amplitude) of an electrical stimulation signal in a discontinuous manner such that stimulation is delivered to patient 52 at one intensity level and then delivered to patient 52 at another intensity level without a "ramp-up" or "ramp-down", such as in a step function. In the second case, there may or may not be a period or time during which no stimulation is being delivered to patient 52. In some examples, IMD 54 (e.g., automatically or in response to instructions from the clinician or patient 52) may reduce the amplitude to some fraction (e.g., in range of 80% to 10%, including 80% or less, 60% or less, 40% or less, or 20% or less) of the amplitude found from the titrating. As used herein, "automatically" means without user intervention or control. In some examples, the IMD 54 may then deliver therapy at the reduced amplitude. In other examples, IMD 54 (e.g., automatically or in response to instructions from the clinician or patient 52) may change the amplitude in a different order that is not consecutively higher or consecutively lower. For example, IMD 54 may deliver stimulation at an amplitude that is 60%, then 20%, then 80%, the 40% of the intensity level threshold of patient 52.

In this manner, IMD 54 may be configured to generate a lower intensity electrical stimulation signal comprising a plurality of pulses, such as a lower energy signal. For instance, the lower intensity electrical stimulation signal has a stimulation intensity that is significantly lower than the intensity level threshold of patient 52. IMD 54 may deliver the lower intensity electrical stimulation signal to the patient. As described, delivery of such lower intensity electrical stimulation signal extends the operational life of IMD 54 and results in efficacious treatment with minimal impact on the quality of life of patient 52.

There may be various ways in which IMD 54 generates the lower intensity electrical stimulation signal. For instance, IMD 54 (e.g., automatically or based on input from a clinician or patient 52) may titrate the intensity down, starting from the intensity level threshold of patient 52, to a first intensity. If patient 52 experiences no pain, IMD 54 may further titrate the intensity down to a second intensity, and so forth until IMD 54 reaches a lower intensity electrical stimulation (e.g., lowest electrical stimulation signal where there is therapeutic result that is below the intensity level threshold of patient 52).

In some examples, after titrating the intensity down, patient 52 may indicate discomfort, unsatisfaction, or pain. In some cases, even under such circumstances, IMD 54 may further titrate the intensity down. After further downward titration in the intensity, patient 52 may again experience therapeutic results.

The reduction in the intensity may be based on a set scale of reduction, In one example, the reduction in the intensity may be based on a set scale of reduction that includes reducing the intensity from, e.g., 80%, to 60%, to 40%, and then to 20%, of the intensity level threshold of patient 52. In an illustrative example, patient 52 may receive stimulation at a first intensity level, and then receive stimulation at a second intensity level. In one example, the first intensity level may be ≥X % of the intensity level threshold of patient 52, and the second intensity level may be <X % of the intensity level threshold of patient 52. "X," in such examples, may be any number selected from the set scale of reduction (e.g., 80%). Patient 52 may receive stimulation at the first intensity level, followed by stimulation at the second, lower intensity level, such that the second intensity level may be effective, or at least more effective, for patient 52.

In some examples, the reduction in intensity may be relatively random (e.g., 80%, then 40%, then 60%, and then 20%, or some other permutation). Reducing the intensity, randomly or otherwise, may be used where a particular patient 52 has a measurable tendency to become accustomed to a particular setting over time and/or accustomed to a change in settings over time, such as a relatively predictable change in settings or a relatively constant change over time. By reducing the intensity of the stimulation signal in a more random manner, treatment may be more effective for the particular patient 52.

In any case, computing device 10 may be implemented as part of system 200 for providing therapy to patient 52 via electrical stimulation. The therapy system 200 may provide, via computing device 10, a neuromodulation trial or SCS therapy to patient 52. Computing device 10 may identify a set of stimulation parameters (e.g., HD parameters, lower charge density parameters, etc.) for the therapy. Computing device 10 may next determine, based at least in part on the set of stimulation parameters 24, one or more efficacy times that correspond to efficacy indicator 22. In an example, computing device 10 may query efficacy indicator database 50 by transmitting characteristics of the therapy program to efficacy indicator database 50 and in return, may receive from efficacy indicator database 50 an efficacy indicator 22 that corresponds to the therapy program. In another example, the efficacy indicator database 50 may receive a signal from IMD 54 with query parameters, including stimulation parameters, timing parameters, location parameters, etc. In turn efficacy indicator database 50 may transfer to computing device(s) 10, e.g., via a computing network, a corresponding efficacy indicator, such as a predicted response profile that is predicted from historical response profiles involving similar or analogous stimulation treatments.

In such examples, computing device 10 may determine efficacy data items 20 for patient 52. Efficacy data items 20 are indicative of a response profile defined by one or more response variables, where the response profile corresponds to the one or more efficacy times of the selected efficacy indicator 22. In addition, computing device 10 may compare the efficacy data items 20 with efficacy indicator 22. Computing device 10 may, in such examples, generate, based on the comparison, an efficacy prediction of long-term efficacy of the electrical stimulation treatment as indicated by an extrapolation of the response profile of patient 52 over time. The extrapolation of the response profile may be informed by the comparison of the response profile to efficacy indicator 22.

Figure 3:
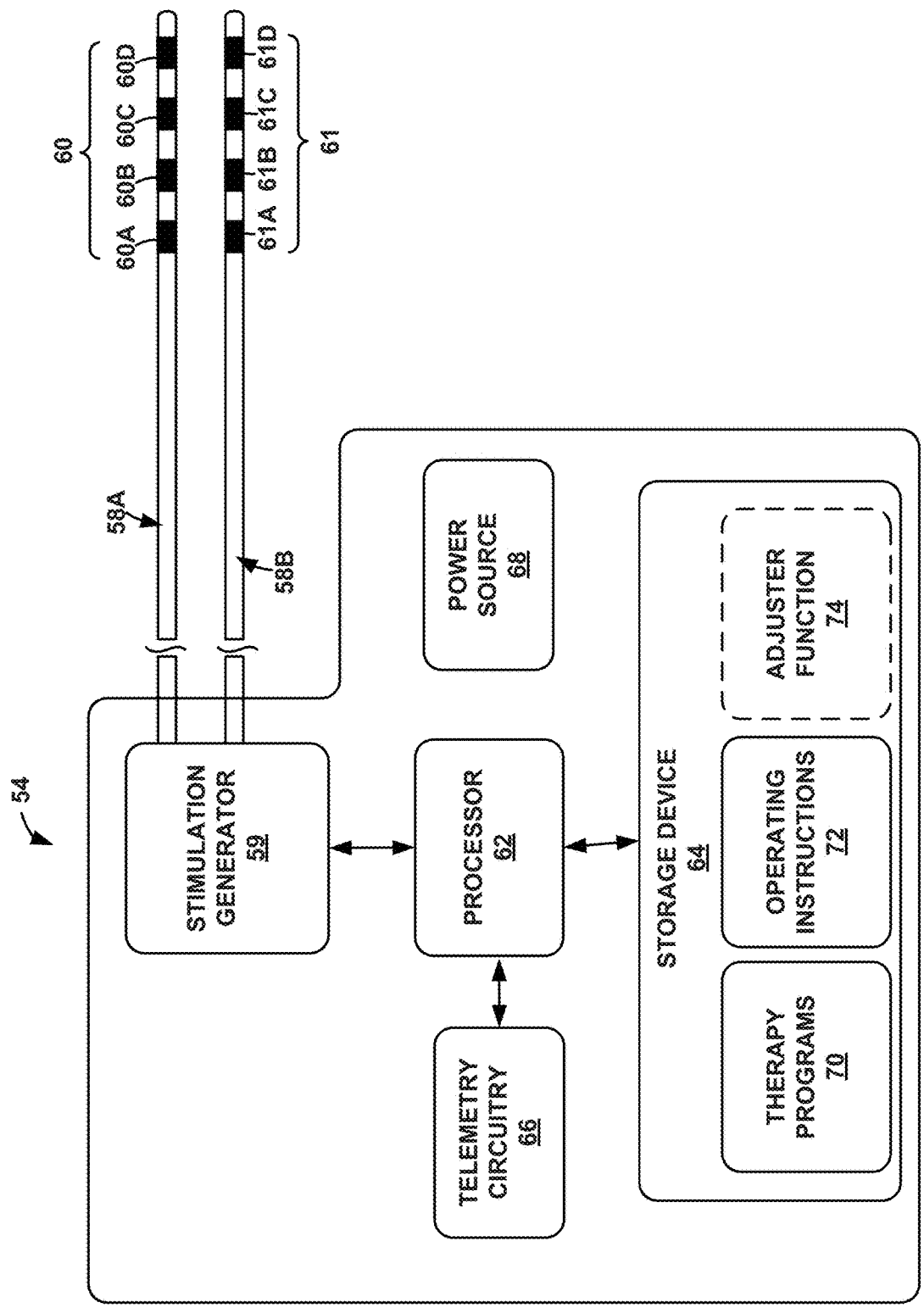
FIG. 3 is a functional block diagram illustrating an example implantable medical device (IMD), such as the IMD described with reference to FIG. 2.

FIG. 3 is a functional block diagram illustrating various components of an example IMD 54. In the example shown in FIG. 3, IMD 54 includes processor 62, storage device 64, stimulation generator 59, telemetry circuitry 66, and power source 68. In other examples, IMD 54 may include a greater or fewer number of components. In some examples, IMD 54 may include sensing circuitry configured to sense one or more patient parameters, one or more inductive coils configured to transfer energy from an external charging device, and/or charging circuitry that manages recharging of power source 68.

Processor 62 is operably connected to and configured to access information from storage device 64 and to control stimulation generator 59 and telemetry circuitry 66. Components described as processor 62 and other processing circuitry of IMD 54, computing device(s) 10, or any other device described in the disclosure, may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. In general, IMD 54 may comprise any suitable arrangement of hardware, alone or in combination with software and/or firmware, to perform the various techniques described herein attributed to IMD 54 and processor 62. In various examples, IMD 54 may include one or more processors 62, such as one or more DSPs, ASICs, FPGAs, programmable logic circuitry, or the like, either alone or in any suitable combination.

Storage device 64 may store therapy programs 70 (or other instructions that specify therapy parameter values for the therapy provided by stimulation generator 59 and IMD 54), operating instructions 72 for execution by processor 62, and any other information regarding therapy of patient 52. In some examples, storage device 64 may also store instructions for communication between IMD 54 and computing device(s) 10, or any other instructions required to perform tasks attributed to IMD 54. In addition, storage device 64 may include adjuster function 74, which may be similar to adjuster function 32 of FIG. 1. IMD 54 may adjust stimulation parameters of therapy programs 70 via adjuster function 74. In some instances, processor 62 may determine a probability function and may cause adjustment to stimulation generator 59 pursuant to an adjustment generated via adjuster function 74. Storage device 64 may include physically separate storage devices, such as for storing therapy programs and operating instructions separately from one another.

Storage device 64 may comprise any suitable storage media, such as RAM, ROM, PROM, EPROM, EEPROM, flash memory, a hard disk, a CD-ROM, comprising executable instructions for causing the one or more processors to perform the actions attributed to them. Although processor 62, stimulation generator 59, and telemetry circuitry 66 are described as being separate, in some examples, processor 62, stimulation generator 59, and telemetry circuitry 66 may be functionally integrated. In some examples, processor 62, stimulation generator 59, and telemetry circuitry 66 may correspond to individual hardware units, such as ASICs, DSPs, FPGAs, or other hardware units.

Stimulation generator 59 forms a device of IMD 54 for delivering therapy via leads 58. In an example, processor 62 may control stimulation generator 59, such that stimulation generator 59 generates and delivers electrical stimulation. In some examples, stimulation generator 59 may generate and deliver electrical stimulation via electrode combinations formed by a selected subset of electrodes 60A-60D, 61A-61D (collectively, "electrodes 60, 61") of leads 58. Stimulation generator 59 may deliver electrical stimulation therapy via electrodes on one or more of leads 58, e.g., as stimulation pulses. Stimulation generator 59 may include stimulation generation circuitry to generate stimulation pulses. In some examples, stimulation generator 59 may include switching circuitry (not shown) to switch the stimulation across different electrode combinations, e.g., in response to control by processor 62. In some examples, stimulation generator 59 may include multiple current sources to drive more than one electrode combination at one time.

In some examples, processor 62 controls stimulation generator 59, for example, by accessing one or more therapy programs 70 from storage device 64 and loading the one or more therapy programs 70 to operate stimulation generator 59. The stimulation parameter values of the stored therapy programs 70 may include, for example, a voltage amplitude, a current amplitude, a pulse frequency, a PW, a duty cycle, a subset of electrodes 60, 61 for delivering the electrical stimulation signal, an electrode configuration, etc. In an example, an electrode configuration includes one or more electrodes 60, 61, from which stimulation generator 59 delivers the electrical stimulation to tissue of patient 52, and polarity or polarities of the one or more electrodes 60, 61.

In some examples, IMD 54 may deliver a sub-threshold electrical stimulation signal to a target tissue site within patient 52 via one electrode combination, such that all pulses are delivered via the same electrode combination. In other examples, IMD 54 may deliver a sub-threshold electrical stimulation signal to a target tissue site within patient 52 via two or more electrode combinations, such that IMD 54 delivers at least two different pulses of a sub-threshold electrical stimulation signal via respective electrode combinations. The delivery of different pulses via respective electrode combinations may help target the electrical stimulation to a target tissue site (e.g., in the case of pain relief, the target may be within 2 mm of a midline of spinal cord 56, for example, and below the T9-T10 spinal disc space). The electrical stimulation delivered by each electrode combination, which may be referred to as a sub-signal, may be interleaved (e.g., delivered at different times) to define the sub-threshold electrical stimulation signal. In some examples, a sub-signal may correspond to a particular therapy program. That is, multiple sub-signals may correspond to therapy programs that are different from one another. In such instances, processor 62 may control stimulation generator 59 to generate and deliver one or more sub-threshold electrical stimulation signals.

Processor 62 may also control the exchange of information with computing device(s) 10 and/or an external programmer using telemetry circuitry 66. Telemetry circuitry 66 may be configured for wireless communication using RF protocols, inductive communication protocols, or any other suitable technique. In some examples, telemetry circuitry 66 may be substantially similar to telemetry circuitry 14 of computing device 10 described herein, providing wireless communication via an RF or proximal inductive medium. To support the wireless communication, telemetry circuitry 66 may include appropriate electronic components, such as amplifiers, filters, mixers, encoders, decoders, etc. Processor 62 may transmit operational information and receive therapy programs or therapy parameter adjustments via telemetry circuitry 66. Also, in some examples, IMD 54 may communicate with other implanted devices, such as stimulators, control devices, or sensors, via telemetry circuitry 66.

In some examples, stimulation generator 59 may generate a lower intensity electrical stimulation signal comprising a plurality of pulses with a stimulation intensity that is significantly lower than the intensity level threshold of patient 52 and deliver the lower intensity electrical stimulation signal to patient 52 through electrode 60 and/or 61. In some examples, IMD 54 delivers electrical stimulation signals with an intensity in the range of 10% to 80% of the intensity level threshold of patient 52. In some examples, IMD 54 delivers electrical stimulation signals with an intensity in the range of 20% to 80% of the intensity level threshold of patient 52. In some examples, IMD 54 delivers electrical stimulation signals with an intensity in the range of 20% to 60% of the intensity level threshold of patient 52. In some examples, IMD 54 delivers electrical stimulation signals with an intensity in the range of 40% to 60% of the intensity level threshold of patient 52. In some examples, IMD 54 delivers electrical stimulation signals with an intensity in the range of 20% to 40% of the intensity level threshold of patient 52. In some examples, IMD 54 delivers electrical stimulation signals with an intensity of approximately 20% of the intensity level threshold of patient 52. In one example, the electrical stimulation signal has a PW of about 90 μs and frequency of about 1000 Hz.

In some examples, processing circuitry, e.g., processor 12 of computing device 10, processor 62 of IMD 54, etc., may determine an efficacy prediction of long-term efficacy in accordance with one or more of the various techniques of this disclosure. Accuracy of the efficacy prediction may be validated based on analysis of efficacy data items (e.g., response variables) obtained at a prospective efficacy time relative to a time of the prediction. In an illustrative example, processing circuitry, e.g., processor 12 of computing device 10, processor 62 of IMD 54, etc., may match a response profile of patient 52 to one or more predetermined response profiles, particular set of response profile characteristics, response indicators, or combinations thereof.

In some examples, processor 12 may identify positive responders of a therapy program by correlating the response profile of patient 52 to known indicators of long-term efficacy. Such correlation can be particularly useful for reducing false negatives, such as might otherwise occur when the short- or mid-term response shows that the therapy is not effective. That is, when considering individual response variables or a response profile, an analysis of particular trends (e.g., short-term trends) between response variables tend to mislead whether a particular therapy is likely to be effective or not if sustained over time. In accordance with techniques of the disclosure, a prediction of long-term efficacy may be based on an efficacy indicator that, in turn, may resolve misleading trends portrayed by changes between response variables as those short term trends may be tracked over time.

In some examples, processor 12 may correlate the response profile of patient 52 with a specific efficacy indicator 22 (e.g., a historical response profile, response profile model, etc.). In such examples, processor 12 may determine one or more times (e.g., efficacy times) during which certain response characteristics align for both the response profile of patient 52 and the efficacy indicator 22 or are otherwise common between the response profile of patient 52 and the efficacy indicator 22. The efficacy indicator 22 may be specific to the therapy characteristics of patient 52. In some examples, processor 12 may, in such instances, determine to correlate the response profile of patient 52 to known indicators of long-term efficacy by updating efficacy indicator 22 based on new data obtained from patient 52 undergoing a therapy that corresponds to efficacy indicator 22. In an example, processor 12 may modify the specific efficacy indicator 22 to include new response characteristics (e.g., response characteristics that were present in the response profile of patient 52 but were not present in the efficacy indicator 22), refine an efficacy time to include a shorter timeframe based on common response characteristics, assign a weight to common response characteristics (e.g., response characteristics that were in both the response profile of patient 52 and the efficacy indicator 22), reinforce data of the efficacy indicator 22 that correspond to positive responders, etc.

Efficacy indicator 22 may indicate the prospective time at which to validate the prediction results or otherwise obtain the additional efficacy data items 20. In addition, the efficacy indicator may indicate additional efficacy times (e.g., prospective or retrospective) for which efficacy data items obtained from a patient may serve as input for prediction. In an illustrative example, efficacy indicator 22 may indicate that at a first efficacy time, a patient may provide pain relief scores as the scores pertain to a pain of patient 52 at the first efficacy time, and may indicate that at a second efficacy time, a reading from a wearable device of the patient may be obtained to serve as an efficacy data item 20 as the reading pertains to a physiological parameter of patient 52 obtained at the second efficacy time. In an example, the wearable device may be configured to measure blood flow at a particular portion of the body of patient 52. In instances where patient 52 is receiving stimulation therapy to increase blood flow to a particular portion of the body of patient 52, a reading of blood flow from the wearable device may serve as an efficacy data item 20. In another example, a wearable device may be configured to measure withdrawal thresholds such as with a von Frey apparatus. Such devices may be particularly useful for patients 52 that are in a particular state of being unable to communicate verbally or otherwise, such as if patient 52 has impaired particular motor functions.

In another example, prediction generator 26 may compare efficacy data items 20 of patient 52 to one or more of efficacy indicators 22 and may provide a prediction of long-term efficacy of the therapy for patient 52. The efficacy data items 20 may include a particular collection of response variables that correspond to as many of the determined efficacy times with which patient 52 may feasibly comply with. That is, particular examples of the disclosure are directed toward determining a developing response profile for patient 52 based on efficacy data items 20, which may include patient pain levels as response variables of the response profile. Efficacy data items 20 may be indicative of specific responses that patient 52 has to the therapy at particular points in time following a start of the therapy. Efficacy data items 20 may be determined in accordance with the one or more efficacy times represented by the efficacy indicator 22. As such, the efficacy prediction may be based on specific responses that patient 52 has to the therapy that coincide with particular segments of an efficacy indicator determined for the therapy. In one example, performing an efficacy prediction may include determining efficacy times that correspond to a particular efficacy indicator 22, where the particular efficacy indicator 22 advantageously corresponds to the therapy of patient 52 (e.g., a therapy program of patient 52 and/or additional therapy characteristics, such as biomarkers of patient 52). The efficacy prediction may further include determining efficacy data items 20 for the patient in accordance with the efficacy times and, in turn, comparing the efficacy data items to one or more of efficacy indicators 22 or in some instances, prompting for additional efficacy data items 20 at subsequent efficacy times.

Figure 4:
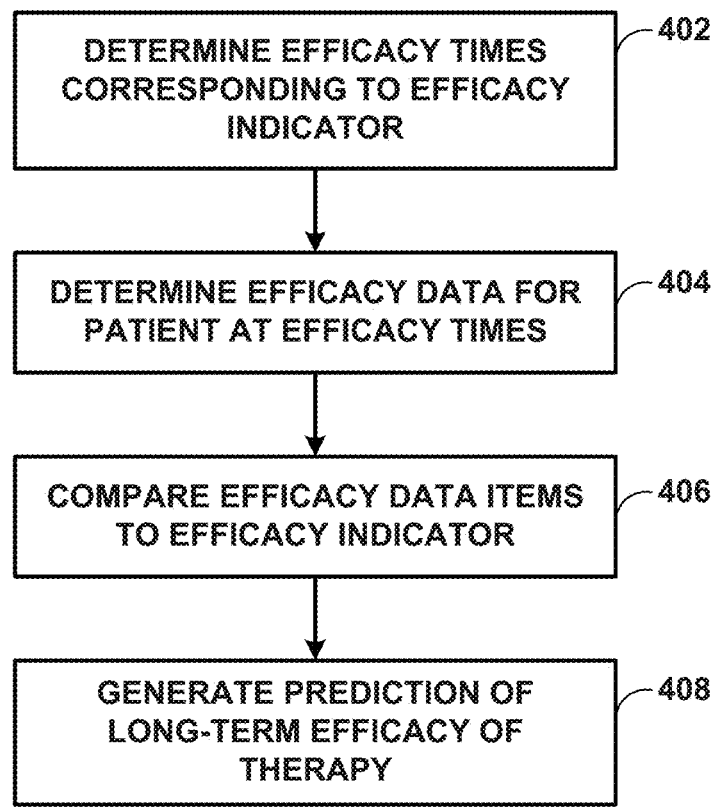
FIG. 4 is a flow diagram of an example method of predicting efficacy of therapy, in accordance with one or more of the various techniques disclosed herein.

FIG. 4 is a flow diagram of an example method of predicting efficacy of therapy, in accordance with one or more of the various techniques disclosed herein. In an example, the method may include providing therapy to patient 52 via electrical stimulation. Although described as being generally performed by computing device(s) 10, the example method of FIG. 4 may be performed by, e.g., any one or more of IMDs 54, a server that, e.g., includes efficacy indicator database 50, etc., such as by processing circuitry of any one or more of these devices. In some examples, processor 12 may perform the functions described with respect to FIG. 4 automatically (e.g., based on a program stored in storage device 16) without a clinician involved or through input received from a clinician (e.g., via UI 18), for example.

In some examples, processor 12 may determine an efficacy indicator 22 that corresponds to a therapy program determined for the patient. Example efficacy indicators 22 may include a predicted response profile, known indicators of long-term efficacy, baseline threshold levels, pre-defined response profiles, predictable response profiles. In general, a response profile is a chronological arrangement of efficacy data items that indicate how a patient is responding to a therapy over time or how historical patients have responded to similar therapies over time. In some examples, efficacy indicator 22 may include one or more of: a predicted response profile, a set of response profile characteristics (e.g., fluctuating, see-sawing, etc.), or one or more response indicators (e.g., efficacy markers, peaks, prolonged peaks, etc.). In general, efficacy indicator 22 indicates a plurality of expected pain relief values spanning a longer time window relative to a shorter time window of a currently developing response profile. That is, prediction generator 26 may generate a prediction as to the likelihood of long-term efficacy of a therapy determined for a patient based on a short-term or mid-term response as the short-term or mid-term response relates to a long-term response represented by a particular efficacy indicator 22. In other words, the long term-efficacy prediction may, in accordance with one or more of the various techniques of the disclosure, be based upon a short-term or mid-term response.

In some examples, processing circuitry, e.g., processor 12 of computing device(s) 10, processor 62 of IMD 54, etc., may determine, relative to a start time of providing the therapy, one or more efficacy times that correspond to an efficacy indicator (402). In an illustrative and non-limiting example, the one or more efficacy times may include an initial response to HD parameters in the first 15 minutes of stimulation and a second phase of positive response starting 48-72 hours later. The efficacy indicator may further demonstrate that the initial response may subside until the second phase.

Processor 12 may determine from efficacy indicator 22 one or more efficacy times. In an example, efficacy indicator 22 may define the efficacy times. In some examples, efficacy indicator 22 may include a list of efficacy times. In another example, processor 12 may determine the one or more efficacy times from efficacy indicator 22 when fetching the efficacy indicator 22 from storage device 16 or from efficacy indicator database 50. In an example, efficacy indicator 22 may include a plurality of historical efficacy data items or a combination of efficacy data items. Processor 12 may analyze efficacy indicator 22 to determine when a positive response variable reached a peak value, an amount of time between peak values, when a negative response correlates with a future positive response, and as such, may determine one or more efficacy times from an analysis of efficacy indicator 22. In an illustrative example, processor 12 may determine, relative to a start time of providing the therapy, the one or more efficacy times as including a first time (e.g., 15 minutes after the start time) and a second time (e.g., 48-72 hours).

In an illustrative example, processing circuitry, e.g., processor 12 of computing device(s) 10, processor 62 of IMD 54, etc., may determine the one or more efficacy times by first determining a set of stimulation parameters (e.g., HD parameters, low frequency parameters with charge densities below an energy threshold, energy levels, etc.) that correspond to therapy program (e.g., therapy programs 70). In an example, processor 12 may determine the one or more efficacy times based at least in part on the set of stimulation parameters 24. Processor 12 may determine the one or more efficacy times from an efficacy indicator that processor 12 selects based on stimulation parameters 24. That is, the relevant parameters for therapy program 70 may be grouped according to similarities between efficacy indicators (e.g., predicted response profiles), and as such, processor 12 may select efficacy indicator 22 from a group that coincides with stimulation parameters 24 determined for patient 52. Processor 12 may then identify a set of efficacy times from efficacy indicator 22 that include where data items of efficacy indicator 22 exceed a particular baseline threshold. Processor 12 may select the baseline value as a clipping baseline to filter out low peaks in pain relief and identify times in which high peaks in pain relief occur.

In an illustrative example, processor 12 may determine that the therapy involves a particular set of HD parameters. Processor 12 may query a database, such as efficacy indicator database 50, for one or more efficacy indicators that corresponds to the therapy of HD parameters. In another example, processor 12 may query storage device 16 for the efficacy indicator or may otherwise obtain efficacy indicator 22 from storage device 16. In some examples, the therapy may include characteristics (e.g., stimulation parameters, lead implantation locations, patient biomarkers) that may correspond to multiple efficacy indicators 22, such as two response profiles obtained pursuant to analogous stimulation parameters and with similar patients. In such instances, however, the two efficacy indicators 22 may not directly align with the current therapy and instead, may be selected from a database as two efficacy indicators 22 that correspond to the current therapy above a matching threshold. In such instances, processing circuitry, e.g., processor 12 of computing device(s) 10, processor 62 of IMD 54, etc., may determine an efficacy indicator 22, or may determine markers of efficacy indicator 22, from the multiple efficacy indicators 22. In any case, processor 12 may output an indication of the one or more efficacy times and receive, via user input, efficacy data items 20 in accordance with the one or more efficacy times.

In such examples, processor 12 (e.g., via prediction generator 26) may identify efficacy indicator 22 based on a correlation between historical response profiles and historical treatment parameters for therapies that have resulted in the historical response profiles. In some examples, processor 12 may further correlate efficacy data items 20 with efficacy indicator 22 and update data corresponding to efficacy indicator 22 to store in efficacy indicator database 50.

In some instances, processing circuitry, e.g., processor 12 of computing device(s) 10, processor 62 of IMD 54, etc., may determine an efficacy indicator 22 anew, such as by interpolating between efficacy indicators 22 or extrapolating from one or more efficacy indicators 22. In an example, processor 12 may determine from efficacy indicator 22 that a prediction based on a comparison involving the efficacy indicator 22 will have a high confidence interval when based upon efficacy data items that correspond with a first efficacy time of 15 minutes and a second efficacy time of 48-72 hours. In addition, processor 12 may determine that the efficacy data items, such as pain relief variables, received from or otherwise determined from the patient include efficacy data items correspond to the first and second efficacy times. In such instances, processor 12 may generate a prediction at a first confidence level based on a comparison of the efficacy data items 20 and efficacy indicator 22.

In an example, processor 12 may compare efficacy data items 20 corresponding to a first efficacy time with a corresponding set of efficacy data items of efficacy indicator 22 to determine how closely the current set of efficacy data items 20 align with the efficacy data items of efficacy indicator 22 at particular times that are measured from a common reference point, such as a start time of electrical stimulation therapy. In another example, efficacy indicator 22 may define, in addition to efficacy times, a threshold for one or more of the efficacy times. In an example, efficacy indicator 22 may, for a particular set of stimulation parameters, define a first efficacy time of 5-15 minutes and a second efficacy time of 48-96 hours. The efficacy indicator 22 may further define a threshold for each or both of the efficacy times, such as a baseline threshold of 150% increase in pain relief. As such, prediction generator 26 may compare efficacy data items 20 collected during the two efficacy times to efficacy indicator 22 that includes the baseline threshold to determine a high likelihood of long-term pain relief where efficacy data items 20 satisfy (e.g., exceed) the baseline threshold at one or both efficacy times.

In another example, computing device 10 may determine the absence of efficacy data items 20 at the first or second determined efficacy times, that the efficacy data items 20 are temporally misaligned, or are otherwise unavailable. Processor 12 may, nevertheless, generate a prediction based on a comparison of the at least one efficacy data item 20 and efficacy indicator 22, but processor 12 may generate the prediction at a second confidence level that is lower relative to the first confidence level. Processor 12 may output confidence levels (e.g., intervals) when outputting the prediction, such as when outputting the prediction via UI 18.

In some examples, processing circuitry, e.g., processor 12 of computing device(s) 10, processor 62 of IMD 54, etc., may determine efficacy data for patient 52 at the one or more determined efficacy times (404). In some examples, the set of efficacy data items 20 may effectively model a short-term response profile for patient 52 undergoing a particular electrical stimulation treatment, such as a developing response profile. In an example, processor 12 may determine, according to the efficacy times, efficacy data items 20 for patient 52. The efficacy data items 20 may be indicative of a response profile defined by one or more response variables (e.g., patient pain levels, pain scores, behavioral changes, etc.). Similarly, efficacy indicator 22 may include historical pain scores in addition to defined efficacy times set out by times in which the pain scores exceed a particular value. In some examples, the efficacy indicator 22 may further define the particular value as a baseline threshold for comparison with efficacy data items 20.

In another example, prediction generator 26 may compare historical efficacy data items of efficacy indicator 22, such as historical or combined pain scores determined over time, with efficacy data items 20 corresponding in time to determine whether the corresponding data items 20 fall within a range of efficacy data items of efficacy indicator 22. The range may be, in an example, a historical efficacy data item at 5 minutes being between 180% and 245% of baseline. Prediction generator 26 may determine an alignment of one of efficacy data items 20 and an efficacy data item of efficacy indicator 22 where, at 5 minutes, an efficacy data item 20 falls within 180% and 245% percent increase in pain relief. Based on this comparison, prediction generator 26 may determine a high likelihood of long-term efficacy, regardless of any dips in efficacy that fall between two efficacy times that are defined by times in which historical efficacy data items exceed a particular threshold (e.g., 150% increase in pain relief).

In some examples, efficacy data item 20 may correspond to patient input provided via UI 18 in response to a prompt for patient 52 to provide feedback on the perceived efficacy of stimulation being delivered via IMD 54. In some examples, processing circuitry, e.g., processor 12 of computing device(s) 10, processor 62 of IMD 54, etc., may identify a specific set of efficacy data items 20, such as behavioral markers, pain relief variables, or other response variables, that coincide with particular efficacy times.

In an illustrative example, before receiving the stimulation treatment, the efficacy times may be determined based on the therapy determined for patient 52. That is, processor 12 may output the efficacy times prior to a start time of the therapy or after the start time of the therapy, such that efficacy data may be obtained during specified time windows. The specified time windows may be known based on an efficacy indicator 22 that corresponds to specific attributes of the therapy (e.g., therapy characteristics). In this way, a particular time window (e.g., a first efficacy time) may not inadvertently pass by before computing device 10 receives a next efficacy data item 20. That is, computing device 10 may determine a prediction as to the long-term efficacy of a therapy based primarily on a particular efficacy data item 20 (e.g., a pain score) collected during a particular efficacy time, such as an initial response. In such instances, failing to receive an efficacy data item 20 during the particular efficacy time would likely result in computing device 10 determining a prediction of long-term efficacy at a relatively low confidence interval. That is, computing device 10 may determine the prediction and additionally, provide an indication as to a confidence interval corresponding to the prediction. In such examples, the confidence interval may fluctuate based on the amount of efficacy data items 20 that have been determined in accordance with the determined efficacy times and likewise, the degree to which particular efficacy times have are missed or that have otherwise passed before computing device 10 receives a next efficacy data item 20.

In an illustrative and non-limiting example, efficacy indicator 22 may indicate that an initial positive response may be expected at the 20 minute mark following the start of the therapy and that the initial response will likely subside at the 25 minute mark. Processor 12 may output the efficacy times, such that efficacy data items are collected at the 20 minute mark precisely, rather than at the 25 minute mark, since a reversal of this specified collection scheme may fool an AI engine trained to determine probability function 28 based on efficacy data items 20. That is, the AI engine may not have efficacy data items 20 that correspond to the 20 minute mark, where the pain relief response may be positive, and instead may only have efficacy data items 20 that correspond to the 25 minute mark, which may be when patient 52 was experiencing a non-response or even a negative response. In such instances, processor 12 may determine that the negative response at 25 minutes is expected and may output an indication as such, but processor 12 may not be able to correct for the lack of efficacy data items 20 at the 20 minute mark because if patient 52 did not experience a positive response as expected during the 20 minute mark, processor 12 would, when comparing efficacy data items 20 at 20 minutes to a corresponding portion of efficacy indicator 22, determine that the likelihood of long-term efficacy is low, whereas if patient 52 did experience a positive response as expected during the 20 minute mark, processor 12 would, when comparing efficacy data items 20 at 20 minutes to a corresponding portion of efficacy indicator 22, determine that the likelihood of long-term efficacy is high or that additional efficacy data should be collected at a second efficacy time (e.g., 25 minutes) in order to validate the accuracy of the efficacy indicator 22 while processor 12 is utilizing efficacy indicator 22 to generate the long-term efficacy prediction.

In some examples, when a particular amount of efficacy data is available, processor 12 may, in some instances, interpolate between measurement data (e.g., efficacy data items) in order to determine one or more interpolated efficacy data items that align with a determined efficacy time (e.g., within an efficacy time window). Processor 12 may perform such an interpolation where portions of the current data may not directly coincide with the efficacy time (e.g., efficacy time window), but where data on either end of the efficacy time may be within a threshold duration of time of the efficacy time. In an example, processor 12 may determine, from a particular efficacy indicator, one efficacy time to occur at a particular hour marker from when the therapy has started. Patient 52, however, may not have been able to provide efficacy data at the particular hour marker. As such, if efficacy data is available both shortly before and shortly after the hour marker, processor 12 may interpolate an efficacy data item to include with a set of efficacy data items. In such instances, processor 12 may identify the interpolated efficacy data as such to signal for prediction generator 26 that the confidence interval for the prediction may be comparatively lower due to processor 12 artificially filling a gap in the response profile of patient 52 identified as coinciding with a determined efficacy time. That is, the gap may specifically occur at a particular time that computing device determines from efficacy indicator 22 as being a time in which collected data may provide a full picture as to a response of patient 52 (e.g., an efficacy time), where the response profile, for particular therapy programs provided patient 52, may be of a fluctuating, see-sawing, or other haphazard nature at particular stages of the therapy (e.g., early stages).

In some examples, processing circuitry, e.g., processor 12 of computing device(s) 10, processor 62 of IMD 54, etc., may compare the efficacy data items 20 with the efficacy indicator 22 (406). In an example, processor 12 may compare the efficacy data items 20 with the efficacy indicator 22. In some examples, processor 12 may determine how closely efficacy data items 20 map onto a predicted response indicated by efficacy indicator 22. In an illustrative and non-limiting example, the predicted response may represent particular times when pain relief is expected to satisfy a pain relief threshold (e.g., a withdrawal threshold). Processor 12 may determine whether efficacy data items 20 satisfy the pain relief threshold at certain times that correspond to efficacy markers of efficacy indicator 22, such as a marker corresponding to an improvement in pain relief that exceeds a predefined threshold.

In another example, computing device 10 may compare efficacy data items 20 to efficacy indicator 22 and generate a prediction of efficacy. In some instances, however, computing device 10 may determine that particular efficacy data items 20 are missing or otherwise do not align with a set of determined efficacy times. In such instances, the computing device 10 may output an indication that the prediction has a lower confidence interval due to missing or misaligned efficacy data items 20. In an illustrative example, computing device 10 may determine treatment information relative to patient 52, such as a set of stimulation parameters 24, energy levels of a stimulation treatment, patient biomarkers, etc. Computing device 10 may determine efficacy indicator 22 (e.g., a predetermined response profile) that corresponds to the treatment information. Computing device 10 may retrieve efficacy indicator 22 from a storage device (e.g., database 50, local storage device 16) that stores a plurality of efficacy indicators 22 that are correlated with treatment information.

In some examples, processor 12 may, based on the comparison, generate a probability function of either a positive (e.g., more pain relief) or a negative (e.g., less pain relief) response to the one or more therapy sessions over a longer period of time. That is, processor 12 may determine such a probability function by comparing the response profile to a predefined response profile. That is, processor 12 may generate, based on the comparison, a probability function, where the probability function is indicative of a likelihood of a particular response to the electrical stimulation manifesting in the patient at a prospective time. In another example, processor 12 may generate, based on the comparison, a probability function, where the probability function is indicative of a likelihood of an expected response to the electrical stimulation treatment manifesting in the patient at a prospective time relative to a start time of a therapy program defining the electrical stimulation treatment. In either case, processor 12 may output, based at least in part on the probability function, a prediction of the long-term efficacy.

In some instances, processing circuitry, e.g., processor 12 of computing device(s) 10, processor 62 of IMD 54, etc., may apply a weighting factor to lower confidence predictions based on probability function 28. In an example, processor 12 may determine, from one or more efficacy indicators 22, a likelihood of the lower confidence prediction being accurate within a predefined threshold, such as based on a determination as to which efficacy data items 20 are missing. In one example, processor 12 may generate a prediction at a fourth efficacy time (e.g., day 7 following the start of treatment), where computing device 10 has determined, from a particular efficacy indicator, that the prediction will have a first confidence interval when based upon a comparison of the efficacy indicator and efficacy data items corresponding to a plurality of preceding efficacy times. Processor 12 may determine, from efficacy indicator 22, that the prediction will have a second confidence interval that is lower than the first confidence interval where a first efficacy data item 20 is unavailable or in some instances, where the first efficacy data items is available but has a quality characteristic (e.g., a signal-to-noise ratio (SNR)) that fails a quality threshold (e.g., a SNR threshold) where the data is indicative of a low quality data capture that is then likely to negatively bias the prediction results and thereby lower the confidence interval of the prediction. Similarly, processing circuitry, e.g., processor 12 of computing device(s) 10, processor 62 of IMD 54, etc., may determine, from efficacy indicator 22, that the prediction will have a third confidence interval that is lower than the first and the second confidence intervals where a second efficacy data item 20 is unavailable or in some instances, where the second efficacy data item 20 is available but has a quality characteristic that fails a quality threshold.

In some examples, processor 12 may generate a readout of an initial response of patient 52 to the stimulation with HD parameters (e.g., an input response) in order to provide an indication of the likelihood that the HD parameters will provide long-term efficacy. The readout may, in some examples, include a positive readout or a negative readout depending on the probability of the response of patient 52 to the HD parameters. In some examples, a positive readout may indicate that the probability of patient 52 exhibiting a positive response over time is relatively high or that the probability of patient 52 exhibiting a negative response over time is relatively low. Similarly, a negative readout may indicate that the probability (e.g., the likelihood) of patient 52 exhibiting a positive response over time is relatively low or that the probability of patient 52 exhibiting a negative response over time is relatively high. In any case, processor 12 may provide a readout (e.g., an output response) that is indicative of the probability of a response of patient 52 to a particular set of stimulation parameters (e.g., HD parameters) over time.

In some examples, processing circuitry, e.g., processor 12 of computing device(s) 10, processor 62 of IMD 54, etc., may generate a prediction of long-term efficacy of the therapy (408). In an example, processor 12 may generate, based on the comparison of the efficacy data items to the efficacy indicator, a prediction of an expected response to the therapy manifesting in the patient at a prospective time. In some examples, processor 12, via prediction generator 26, may generate the prediction based on probability function 28. That is, processor 12 may determine probability function 28 based on the comparison, which may in turn, indicate a likelihood of long-term efficacy of the therapy for patient 52. In an example, probability function 28 may be indicative of a likelihood that the expected response to the electrical stimulation manifests in patient 52 at a prospective time. That is, the probability function may be indicative of the likelihood that a set of stimulation parameters (e.g., HD parameters) will provide long-term efficacy. In such examples, processing circuitry, e.g., processor 12 of computing device(s) 10, processor 62 of IMD 54, etc., may determine probability function 28 based on a comparison of efficacy indicator 22 to efficacy data items 20. Depending on the amount and degree of similarities and differences between the predicted response (e.g., efficacy indicator 22) and the actual response thus far, processor 12 may determine how likely the particular therapy program 70 will manifest in a long-term positive result for patient 52.

In another example, prediction generator 26 may utilize one or more efficacy indicators to generate a prediction as to the long-term efficacy of a particular therapy. Prediction generator 26 may generate the prediction based on a particular set of efficacy data items 20 (e.g., resultant efficacy inputs, response variables, pain relief variables, etc.) that correspond to specific efficacy times determined from the one or more efficacy indicators. In general, the prediction may indicate a likelihood that a particular therapy, if sustained over time, may result in the manifestation of a particular response to the therapy at various moments in time (e.g., prospective times).

Figure 5:
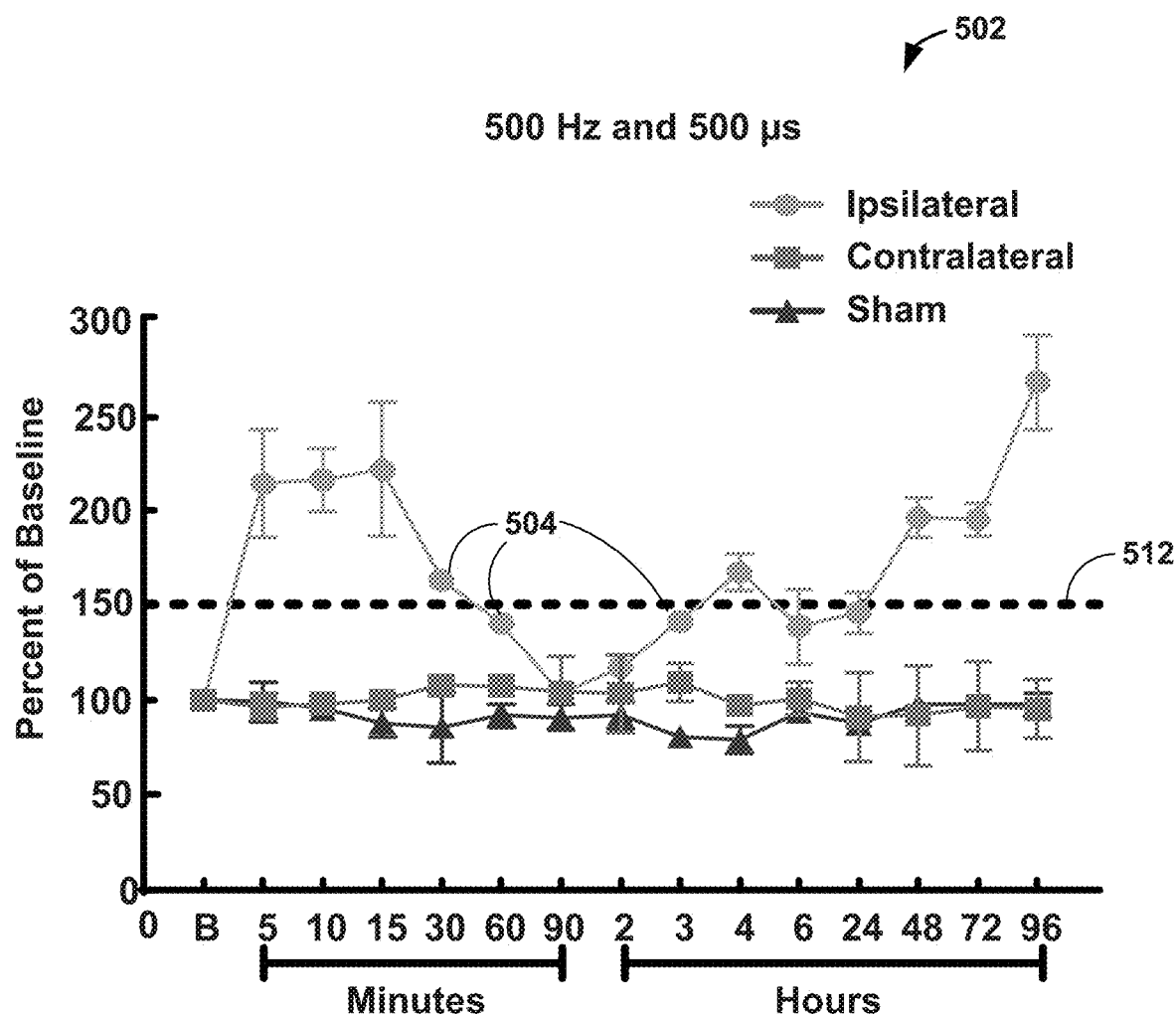
FIG. 5 is an illustration of an example response profile pursuant to a therapy session including particular therapy characteristics, in accordance with one or more of the various techniques disclosed herein.

FIG. 5 is an illustration of an example response profile 502 pursuant to a therapy session including particular therapy characteristics, in accordance with one or more of the various techniques disclosed herein. Response profile 502 provides an example in which a withdrawal response to SCS at parameters of 500 Hz, 500 µs, 50% MT were bi-phasic with an initial peak at 10 minutes of stimulation and a second peak starting at 48 hours of stimulation. The dashed black line 512 depicts a 50% increase in withdrawal threshold. In such examples, processor 12 may determine that efficacy data items 504 SCS, at greater charge, produces biphasic effect (e.g., a fluctuating behavior). Efficacy data items 504 may be examples of efficacy data items 20. In an example, processor 12 may determine efficacy data items 504 from user input, such as pain relief values that correspond to particular efficacy times. Processor 12 may store the pain relief values (e.g., recorded pain scores) of patient 52 with an indication as to when in time the pain relief values were determined relative to the start time of the therapy. In the example of FIG. 5, IMD 54 has delivered 96 hours of electrical stimulation to the spinal cord of patient 52 for the treatment of pain and efficacy data items 504 have been collected at various intervals as indicated on the x-axis, where a subset of the times include determined efficacy times (e.g., 5-10 minutes in this example, 48-96 hours). That is, response profile 502 represents a developing response profile as represented by efficacy data items 504 over time.

FIG. 5 also illustrates a sham response profile and contralateral response profile for patient 52 to provide references that illustrate the bi-phasic nature of the response on a side being treated for pain relief (e.g., the ipsilateral side in this example). Response profile 502 illustrates the results of an experimental study, in which a test subject developed response profile 502 over time. Response profile 502 may be compared to efficacy indicator 22, such as an efficacy indicator that corresponds to a 500 Hz and 500 µs treatment, to determine whether a bi-phasic effect aligns with a predicted response profile of a selected efficacy indicator 22.

In some examples, processor 12 may compare efficacy data items 504 with efficacy indicator 22 may correlate efficacy data items 504 to a predicted response profile (not shown) to determine alignment of the efficacy data items with one or more portions of the predicted response profile that correspond to the efficacy times. The one or more portions may include peaks of a predicted response profile (e.g., efficacy indicator), such as bi-phasic with an initial peak at 10 minutes of stimulation and a second peak starting at 48 hours of stimulation. That is, processor 12 may correlate measured response profile 502 to a predicted response profile (e.g., efficacy indicator 22), such as a pre-defined response profile retrieved from efficacy indicator database 50.

In some examples, processor 12 may, in addition, compare an analysis based on short-term trends of, e.g., response profile 502, against a long-term efficacy prediction based on long-term efficacy predictors (e.g., an efficacy indicator selected based on particular therapy parameters or characteristics) to determine a difference between such different prediction analyses. Processor 12 may output the difference between such predictions to a healthcare professional (HCP) or AI engine and/or ML model to inform a decision as to whether adjustment of the therapy is possible to achieve greater long-term efficacy or whether a new therapy model should be employed for treatment of the patient. Otherwise, processor 12 may similarly output the long-term efficacy prediction that was based on long-term efficacy predictors. Processor 12 may utilize the prediction in order to adjust the therapy parameters, sustain the therapy into the long-term period that follows the short-term period, or employ a new therapy model for patient 52 altogether. such as when the long-term efficacy prediction has a higher confidence interval compared to the analysis based on short-term trends. In such examples, may automatically select a therapy program in response to correlating the response profile to known indicators of long-term efficacy.

In some examples, processor 12 may determine a response profile, such as an initial response profile 502 or initial response, of patient 52 following one or more therapy sessions. The one or more therapy sessions may be performed using a particular set of stimulation parameters (e.g., HD parameters). In such examples, processor 12 may determine an efficacy indicator, such as a predefined response profile, that corresponds to the particular set of stimulation parameters. In an example, processor 12 may processor 12 may compare the response profile to a predefined response profile (e.g., a baseline threshold level).

In some examples, processor 12 may store response profile 502 to efficacy indicator database 50, such as storage device 16, or another storage device of, for example, a data server. Processor 12 may tag response profile 502 with metadata (e.g., stimulation parameter data), such that response profile 502 may be used as a historical response profile for future comparisons involving other patients receiving analogous therapy (e.g., of a same group of therapies, etc.). In another example, efficacy time information may be extracted prior to storing response profile 502 to efficacy indicator database 50, such that the efficacy time information is stored, rather than all efficacy data items that represent response profile 502. In an illustrative example, processor 12 may store to efficacy indicator database 50, for subsequent retrieval to perform additional efficacy predictions, an indication that, under similar treatment circumstances, a bi-phasic response profile can be predicted to result with a particular amount in between phases or where each phase aligns with particular efficacy times. In particular, processor 12 may indicate, as part of the efficacy time information, that at a first efficacy time of 10 minutes with 5 minute time window on either side, a first positive response can be predicted to occur and at a second efficacy time of 48 hours to 96 hours a second exponential increase can be predicted to occur. Processor 12 may cross reference such observations against other efficacy indicators 22 that correspond to similar stimulation treatments to determine how common the observations are across different efficacy indicators 22.

Figure 6:
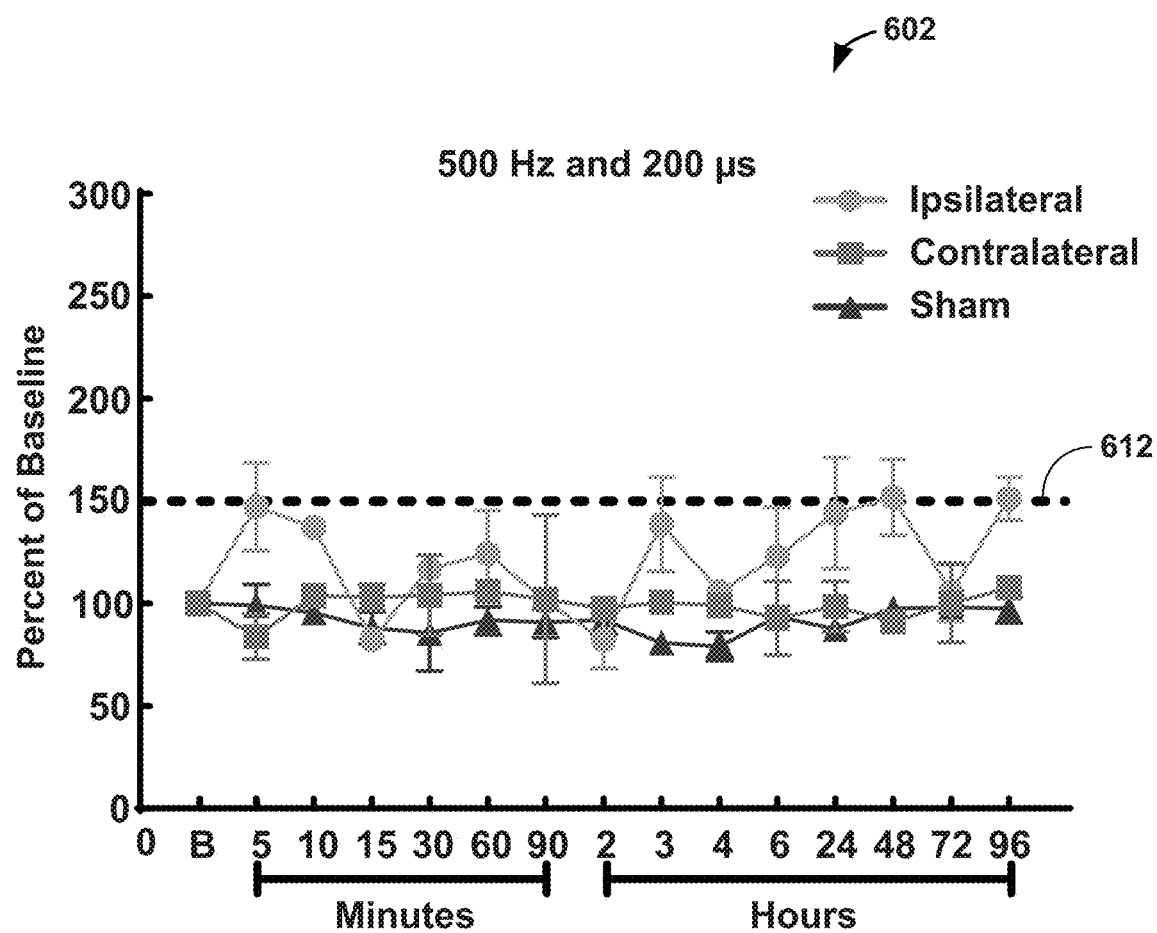
FIG. 6 is an illustration of an example response profile pursuant to a therapy session including particular therapy characteristics, in accordance with one or more of the various techniques disclosed herein.

FIG. 6 is an illustration of an example response profile 602 pursuant to a therapy session including particular therapy characteristics, in accordance with one or more of the various techniques disclosed herein. In the example, the stimulation therapy involved delivery of 500 Hz and 200 µs treatment. In this example, processor 12 may determine that a lack of effect in the first 5-15 minutes yields no significant effect throughout the observation period (through hour marker 96). In such examples, processor 12 may determine that an absence of a peak effect in the first 15 minutes could predict the lack of efficacy moving forward. That is, prediction generator 26 may, when analyzing efficacy indicators for such stimulation therapy treatments, may determine that a lack of pattern in the predicted response profile may allow an early prediction as to efficacy based on an efficacy data item at an early time not satisfying a predefined threshold 612.

Figure 7:
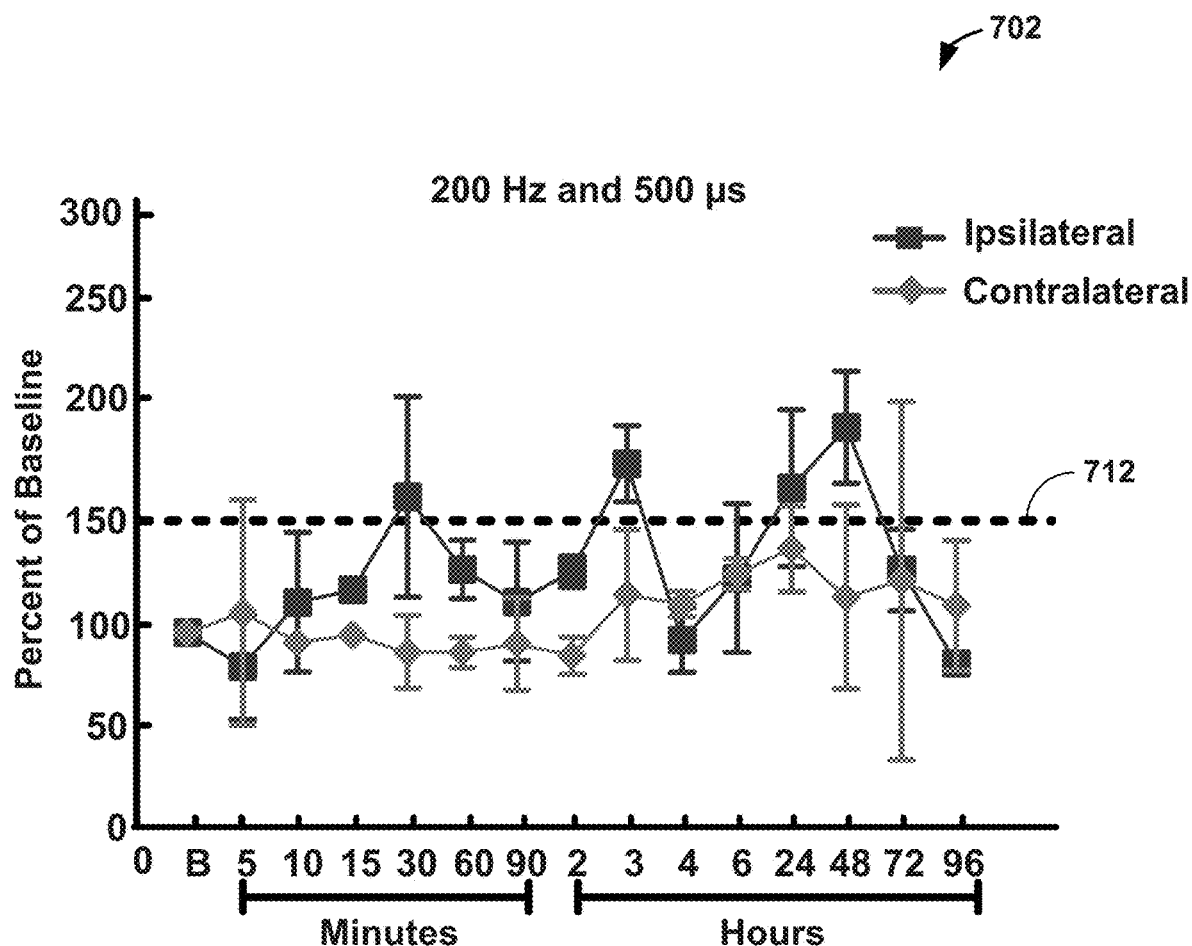
FIG. 7 is an illustration of an example response profile pursuant to a therapy session including particular therapy characteristics, in accordance with one or more of the various techniques disclosed herein.

FIG. 7 is an illustration of an example response profile pursuant to a therapy session including particular therapy characteristics, in accordance with one or more of the various techniques disclosed herein. In the example, the stimulation therapy involved delivery of 200 Hz and 500 µs treatment. In this example, processor 12 may determine that a delay of positive response until the first efficacy marker (e.g., peak at 30 minute efficacy time in this example) may not be indicative of a likelihood of long-term efficacy because the efficacy indicator 22 may indicate that first efficacy time is not until 30 minutes and that if efficacy data is collected at 15 minutes or 60 minutes, the efficacy data will not be very useful in determining what the effect is at the efficacy time of 30 minutes. This is especially true where the margin of passing threshold 712 is predicted to be very small at the first efficacy time, in which case missing the efficacy time could be detrimental to accurately determining efficacy until a subsequent efficacy time (e.g., hour 3 in this example).

In this example, processor 12 may determine an efficacy indicator 22 having a see-saw pattern of effect with multiple peaks or in instances of predicting efficacy, may compare efficacy data items during such predicted peaks to determine an efficacy prediction for patient 52 receiving such electrical stimulation treatment. With this parameter set, processor 12 may observe two additional peaks at 3 hours and 72 hours. In such instances, processor 12 may utilize efficacy indicator 22 that indicates such a see-saw pattern when evaluating efficacy data items received pursuant to such electrical stimulation parameters.

Figure 8:
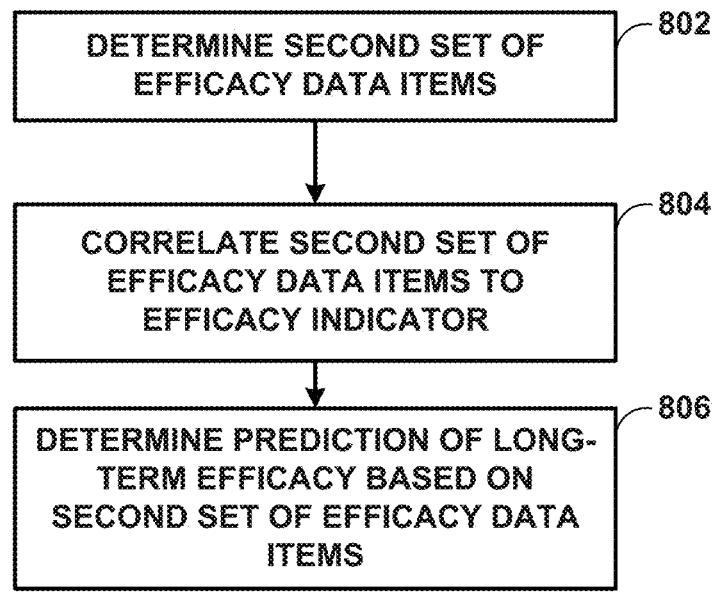
FIG. 8 is a flow diagram of an example method of predicting efficacy of a therapy based on particular sets of efficacy data items obtained at variously specified points in time, in accordance with one or more of the various techniques disclosed herein.

FIG. 8 is a flow diagram of an example method of predicting efficacy of a therapy based on particular sets of efficacy data items obtained at variously specified points in time, in accordance with one or more of the various techniques disclosed herein. The efficacy data items may comprise a first set of efficacy data items that correspond to a first efficacy time and a second set of efficacy data items that does not correspond to a time signified by processor 12 as being an efficacy time (e.g., an intermediate time). Processor 12 may determine the second set of efficacy data items for patient 52 (802). The second set of efficacy data items corresponds to an intermediate time that separates a plurality of efficacy times. Processor 12 may correlate the second set of efficacy data items to the efficacy indicator to determine alignment of the second set of efficacy data items with an intermediate portion of the efficacy indicator that corresponds to the intermediate time. In addition, processor 12 may determine, based at least in part on the correlation of the second set of efficacy items to the efficacy indicator, a prediction of a expected response.

In an illustrative example, the one or more efficacy times may include at least one first efficacy time in which a first response variable of the one or more response variables (e.g., efficacy data items) is expected to satisfy a first efficacy threshold, and at least one second efficacy time in which a second response variable of the one or more response variables is expected to satisfy a second efficacy threshold. In such examples, an amount of time separates the at least one first efficacy time and the at least one second efficacy time during which a third response variable is expected to reflect a lower pain relief value relative to pain relief values corresponding to the at least one first efficacy time or the at least one second efficacy time. The efficacy indicator may, in such examples, include a first set of expected efficacy metrics that define a first efficacy threshold, and a second set of expected efficacy metrics that comprise a difference amount relative to the first set of expected efficacy metrics. That is, the difference amount defines a second efficacy threshold. In such examples, processor 12 may compare the efficacy data items with efficacy indicator 22 by comparing efficacy data items 20 with the first efficacy threshold or the second efficacy threshold. In addition, processor 12 may generate the prediction by determining, from the comparison, a proximity metric of the efficacy data items relative to the first efficacy threshold or the second efficacy threshold. Processor 12 may generate the prediction based on the proximity metric. In this way, the pain relief in an expected high relief windows could be measured either relative to the pain relief in a dip time window, or as an absolute (e.g., if it is a high enough pain relief score, the dip becomes irrelevant), where these relative differences and absolute values are represented by various efficacy metrics and proximity metrics. The metrics may, in some instances, defined by efficacy indicator 22. In any case, processor 12 may determine a first set of expected efficacy metrics that satisfy a particular efficacy threshold, and a second set of expected efficacy metrics that comprise a difference amount relative to a value of the first set of expected efficacy metrics, wherein the difference amount satisfies a second efficacy threshold.

Figure 9:
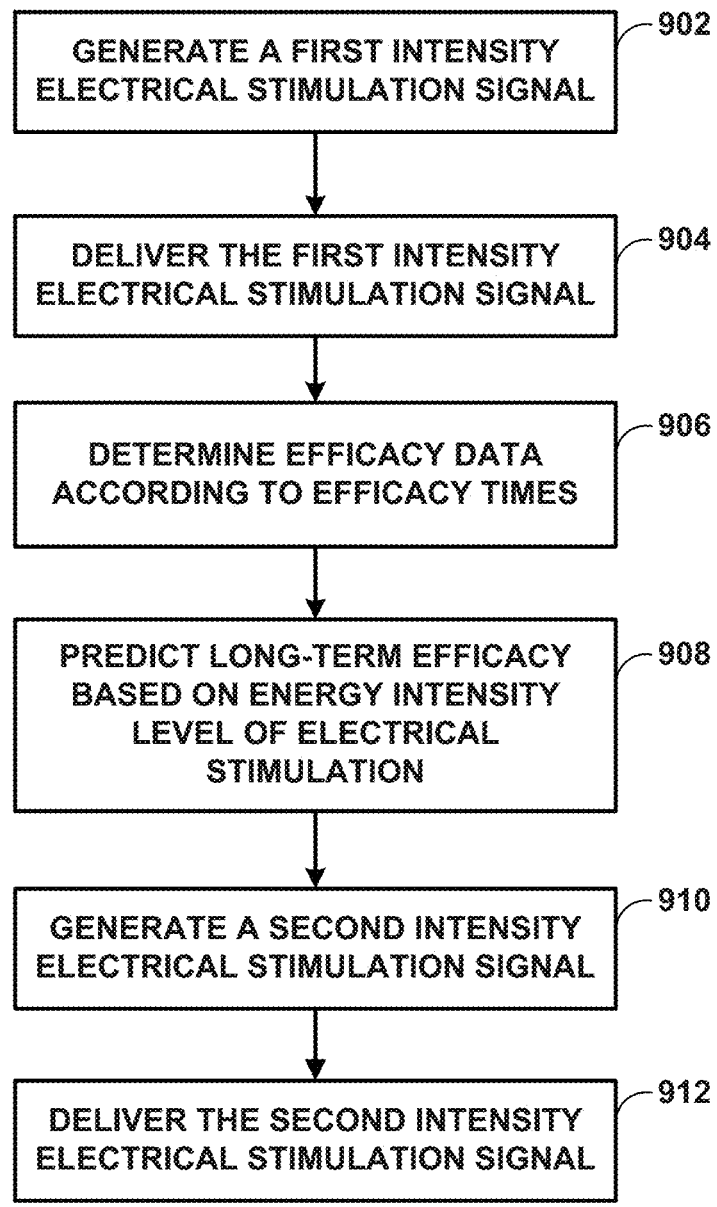
FIG. 9 is a flow diagram of an example method of adjusting intensity levels of a therapy based on a long-term efficacy prediction, in accordance with one or more of the various techniques disclosed herein.

FIG. 9 is a flow diagram of an example method of adjusting intensity levels of a therapy based on a long-term efficacy prediction, in accordance with one or more of the various techniques disclosed herein. The electrical stimulation parameter values with which IMD 54 may generate and deliver the sub-threshold electrical stimulation described herein may be selected using any suitable technique. FIG. 9 is a flow diagram of an example technique for titrating to select the electrical stimulation parameter values. While FIG. 9 is described with respect to processor 62 of IMD 54, in other examples, processor 12 of computing device(s) 10 may perform any part of the technique described with respect to FIG. 9, alone or in combination with processor 62 of IMD 54. Also, while FIG. 9 is described with a certain number of titrations, any number may be used. In some examples, the technique of FIG. 9 may be utilized to attempt to titrate to an ideal intensity electrical stimulation signal for a given patient, for example, patient 52.

In the technique shown in FIG. 9, processor 62 generates a first intensity electrical stimulation signal for patient 52 (902), e.g., by retrieving a stored paresthesia or perception threshold intensity level from storage device 64, or by receiving a paresthesia or perception threshold intensity level from another device, e.g., computing device(s) 10, from for example a physician or clinician. Processor 62 may, for example, determine the paresthesia threshold, determine the perception threshold, determine the lower of the paresthesia threshold intensity level or the perception threshold intensity level for patient 52, or determine the higher of the paresthesia threshold intensity level or the perception threshold intensity level for patient 52.

A paresthesia threshold intensity level may be a lowest determined electrical stimulation intensity level at which patient 52 first perceives paresthesia from the electrical stimulation delivered by IMD 54. A perception threshold intensity level may be a lowest determined electrical stimulation intensity level at which patient 52 first perceives the electrical stimulation delivered by IMD 54. In some cases, depending on the patient and/or the target electrical stimulation site within the patient, the patient may first perceive the electrical stimulation delivered by IMD 54 as paresthesia. Thus, in some cases, the perception threshold intensity level may be substantially the same (e.g., identical or nearly identical) as the paresthesia threshold intensity level. In other cases, however, patient 52 may first perceive the electrical stimulation as a sensation different than paresthesia. Thus, in some cases, the perception threshold intensity level may be different than the paresthesia threshold intensity level. In these examples, a clinician may program IMD 54 and/or computing device(s) 10 to use either the perception or paresthesia threshold intensity levels to select the electrical stimulation parameter with the technique shown in FIG. 9.

After determining one or both of the paresthesia threshold intensity level or the perception threshold intensity level, processor 62 may control stimulation generator 59 to deliver a first intensity electrical stimulation signal (904). The first intensity electrical stimulation signal, may be a sub-threshold electrical stimulation signal. IMD 54 may deliver the first intensity electrical stimulation signal to the patient 52 through one or more of the electrodes 60 and 61.

In some examples, processor 62 scales one or more of the amplitude, pulse width or frequency from the electrical stimulation signal used to determine the paresthesia threshold or perception threshold to generate parameters for the first intensity electrical stimulation signal. In some examples, processor 62 may utilize a strength-duration curve to determine these parameters. An example of a strength duration curve is an amplitude-pulse width curve. The amplitude-pulse width curve may reflect, for a selected stimulation frequency, different combinations of amplitude and pulse width values that contribute to a stimulation field in a substantially similar manner. For example, the amplitude-pulse width curve may indicate that a first electrical stimulation signal with a first amplitude and a first pulse width, and a second electrical stimulation signal having a higher amplitude pulse with a shorter pulse width (i.e., shorter than the first pulse width) may both provide electrical stimulation therapy below the paresthesia or perception threshold of patient 52. Each position on the amplitude-pulse width curve, or each position within a particular range of positions along the amplitude-pulse width curve, may result in a substantially similar stimulation energy when the other therapy parameter values, such as a frequency, remain substantially constant (e.g., the other therapy parameter values may remain within a particular range of therapy parameter values, such as within a 10% window or less from the values defined by the therapy program). Thus, for a given stimulation frequency, the amplitude-pulse width curve may define, e.g., via the amplitude-pulse width combinations associated with the area under the curve and/or along the curve, the amplitude and pulse width combinations that provide electrical stimulation therapy having an intensity level below the paresthesia or perception threshold intensity level of patient 52.

After a first period of time, processor 62 may determine, in accordance with the one or more determined efficacy times, efficacy data pertaining to the first intensity electrical stimulation signal (906). Processor 12 or processor 62 may then determine, based on the efficacy data, a prediction of long-term efficacy (908). In some examples, an adjuster function 32 may titrate therapy according to probability function 28. A negative readout would trigger an adjustment of parameters that would trigger a change in the therapy program, such as a change in stimulation parameters 24. In such examples, processor 12 may determine, based on the prediction, an adjuster function. Processor 12 may then apply the adjuster function to adjust the therapy in response to the prediction. That is, processor 12 or processor 62 may titrate therapy according to the probability function, such as in response to the prediction indicating that there is low probability of long-term efficacy manifesting in patient 52. In another example, processor 12 or processor 62 determine, based on the efficacy prediction, an adjuster function and may apply the adjuster function to adjust the set of stimulation parameters in response to the efficacy prediction.

Where the probability of long-term efficacy is low, processor 12 or processor 62 may determine to adjust the stimulation signal. Processor 12 or processor 62 may generate a second intensity electrical stimulation signal (e.g., generate parameters for an electrical stimulation signal) (910). IMD 54 may then deliver a second intensity electrical stimulation signal to the patient 52 through one or more of the electrodes 60 and 61 (912), such as when the probability of long-term efficacy is determined to be low based on the efficacy data determined for the first intensity electrical stimulation signal.

In some examples, processor 12 may determine a second probability function, in a similar manner to the above, but for the adjusted parameters. That is, processor 12 may assess a second probability function based on the adjusted parameters and a second set of efficacy data items (e.g., response variables obtained at a prospective time). Depending on whether the second probability function indicates a negative or positive response outlook, processor 12, via adjuster function 32, may titrate therapy once again based on the adjusted parameters and/or based on the second probability function.

Figure 10:
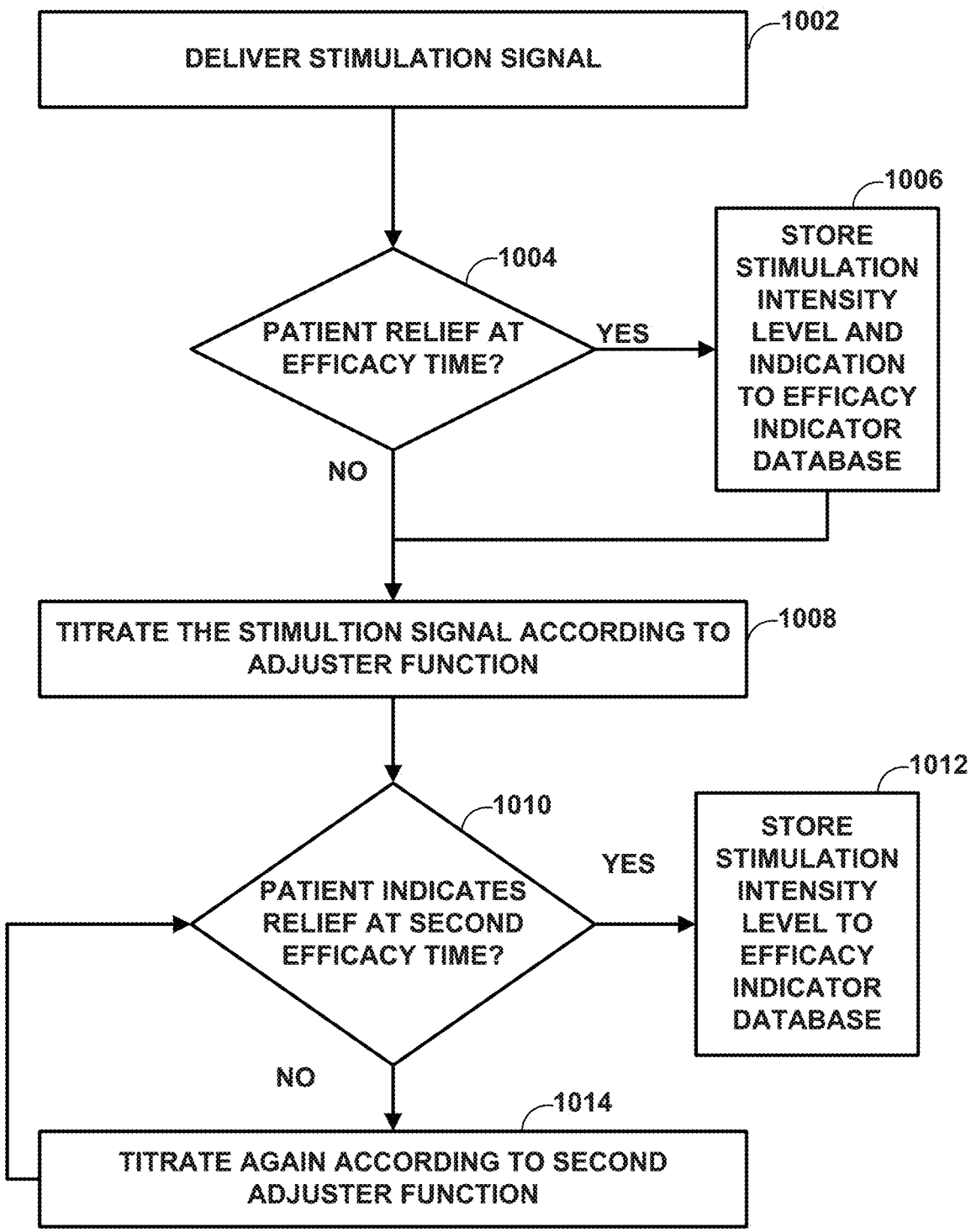
FIG. 10 is a flow diagram of an example method of adjusting therapy characteristics and systematically populating an efficacy indicator database, in accordance with one or more of the various techniques disclosed herein.

FIG. 10 is a flow diagram of an example method of adjusting therapy characteristics and systematically populating efficacy indicator database 50, in accordance with one or more of the various techniques disclosed herein. When titrating between different stimulation signal intensities as described above with respect to FIG. 9, it may be desirable to enable patient 52 to provide input on computing device(s) 10, for example, on their level of discomfort or dissatisfaction (e.g., efficacy data items). Processor 62 of IMD 54 may take the input from computing device(s) 10 and automatically take action based on that input (e.g., sustain or adjust stimulation parameters). For example, processor 62 may cause stimulation generator 59 to deliver a stimulation signal of a particular intensity to patient 52 through electrodes 60 and/or 61. Processor 12 may then determine patient data items at particular efficacy times (1004). Processor 62 may then determine, from a comparison with an efficacy indicator whether or not patient 52 is likely to experience long-term relief. If patient 52 indicates pain relief, via UI 18, on computing device(s) 10, for example, processor 62 may store the current intensity level and the efficacy data items in storage device 64 and/or to efficacy indicator database 50 (1006). If not, processor 62 may titrate that stimulation to another intensity level, such as based on adjuster function 32 (1008). Processor 62 may then await input from patient 52, for example, such as whether or not patient 52 experiencing discomfort or is the patient dissatisfied with the treatment (1010).

If patient 52 indicates pain relief, via UI 18, on computing device(s) 10, for example, processor 62 may store the current intensity level and the efficacy data items in storage device 64 and/or to efficacy indicator database 50 (1012). In some examples, processor 62 may titrate the stimulation signal again based on a second adjuster function 32, such as where the second probability function indicates again a low probability of long-term efficacy based on the updated stimulation parameters (1014).

Processor 62 may perform the functions described with respect to FIG. 10 automatically (e.g., based on a program stored in storage device 64) without a clinician involved or through input from a clinician using computing device(s) 10, for example.

In an illustrative example involving experimental data (e.g., FIGS. 5-7 and 11-13) patient 52 may receive IMD 54 (e.g., an SCS implant) in order to alleviate pain caused by the peroneal nerve of patient 52. In some examples, an apparatus, such as an automated von Frey apparatus, may be used to perform Quantitative Sensory Testing (QST) on patient 52 to determine an efficacy of one or more therapy programs. In an example, a 1000 g von Frey apparatus may be applied to a lateral surface of the leg of patient 52 in an area of innervation of the sural nerve of patient 52. The maximum force applied at which patient 52 withdraws from the tip is measured electronically and documented.

In an exploratory study, a SCS therapy model was developed in chronically hypersensitized test subjects. The SCS therapy model was used to test several clinically-relevant parameters. In one study, the effects of continuous stimulation at 500 Hz and 500 μs over a period of 5 days were monitored.

In some examples, processor 12 may link efficacy indicators (e.g., historical response profiles) to the amount of energy being delivered. That is, the use of higher frequencies and PWs injects a greater amount of energy or charge into spinal cord 56. The specific frequency and PW, however, may be varied with similar results, so long as the total amount of delivered energy remains similar. In such examples, processor 12 may determine an energy level corresponding to the set of stimulation parameters; and determine the one or more efficacy times based at least in part on the energy level.

In some examples, processor 12 may determine a correlation between a first set of efficacy data items and the energy level. Processor 12 may then generate, based at least in part on the correlation, a baseline threshold level. In addition, processor 12 may determine a second set of efficacy data items and compare the second set of efficacy data items with the baseline threshold level. The second set of data items may correspond to a different patient than patient 52, where the first set of efficacy data items may correspond to patient 52. In such examples processor 12 may generate an initial response indicator comprising a positive readout, where the positive readout indicates a probability of a positive response, and where the probability satisfies a positive response threshold.

In some examples, processor 12 may update efficacy indicator database 50 based on identified positive responders in efficacy indicators. In an example, processor 12 may (a) determine, from efficacy data items, positive and negative response data relative to a stimulation treatment, (b) determine a baseline based on the response data, (c) determine stimulation parameters for a particular stimulation treatment for a patient, (d) determine the baseline, wherein the baseline corresponds to one or more values of the stimulation parameters (e.g., an energy level), (e) determine efficacy time windows from the baseline, and (f) outputting an indication of the efficacy time windows that prompts a patient or physician to collect, e.g., pain scores during those time windows. Processor 12 may, based on the indication, prompt the physician or patient 52 to collect pain scores in a particular manner, such as to collect high point and low point efficacy data items during each efficacy time window or during particular time windows, such as when the efficacy indicator includes a so-called candlestick data set.

Figure 11:
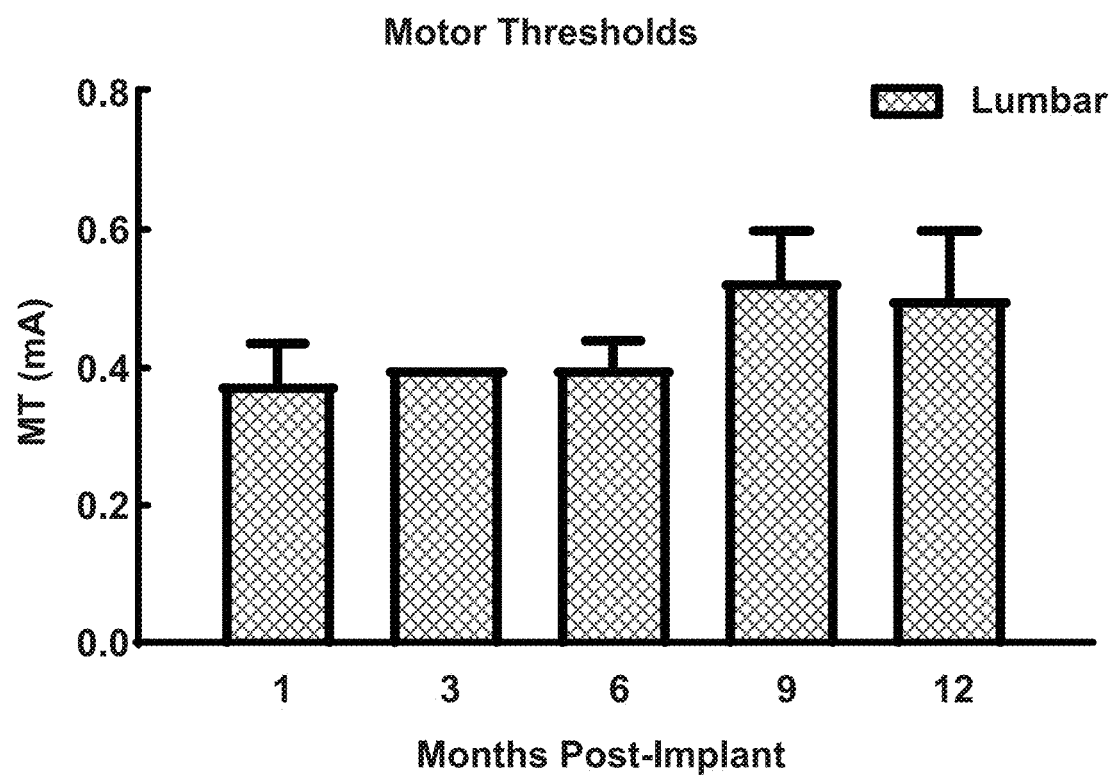
FIG. 11 is a chart illustrating example response data indicative of a patient response to therapy over time, in accordance with one or more of the various techniques disclosed herein.

FIG. 11 is a chart 1102 illustrating example response data indicative of a patient response to therapy over time, in accordance with one or more of the various techniques disclosed herein. Chart 1102 illustrates how motor thresholds (MT) were tested to confirm location and viability of the leads (FIG. 11).

Figure 12:
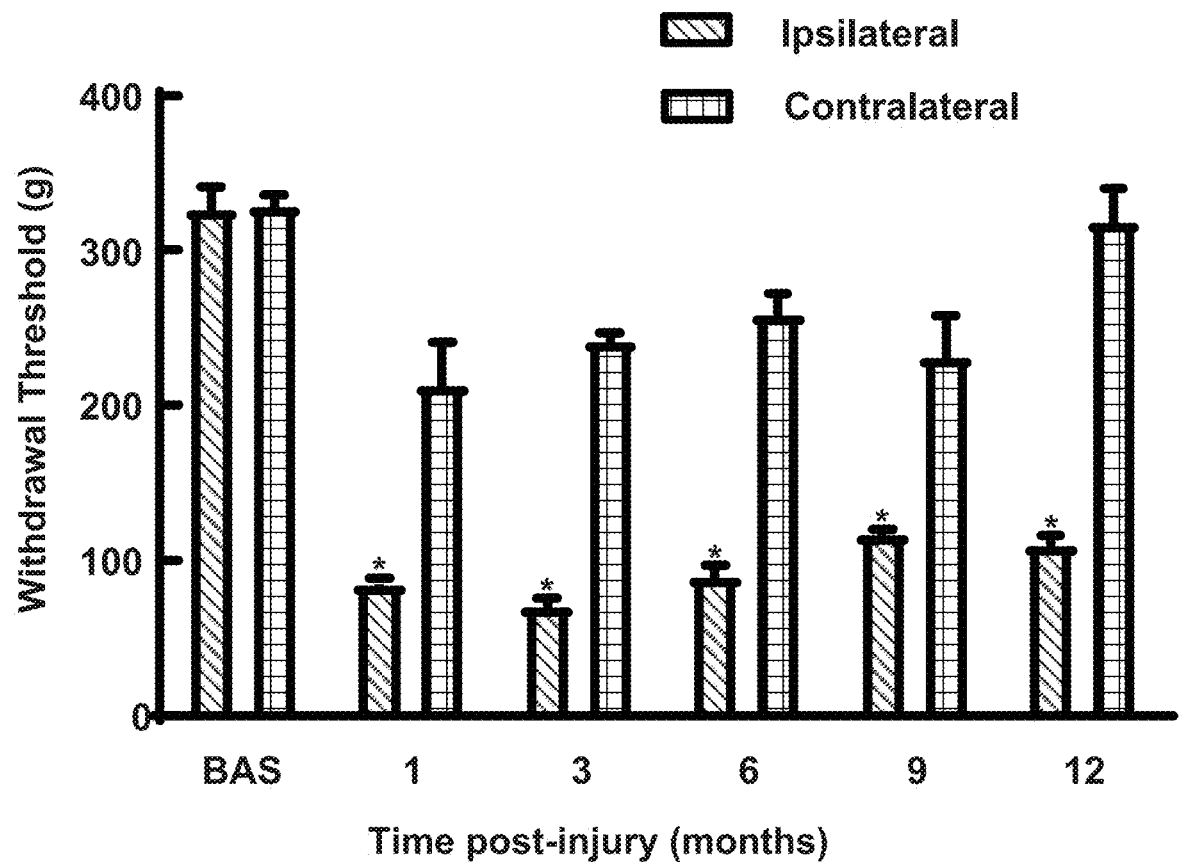
FIG. 12 is a chart illustrating example response data indicative of a patient response to therapy over time, in accordance with one or more of the various techniques disclosed herein.

FIG. 12 is a chart 1202 illustrating example response data indicative of a patient response to therapy over time, in accordance with one or more of the various techniques disclosed herein. Chart 1202 illustrates how a particular one of patients 52 sustained a hypersensitive state for 12 months as compared to the uninjured contralateral hindlimb (*$P<0.05$).

Figure 13:
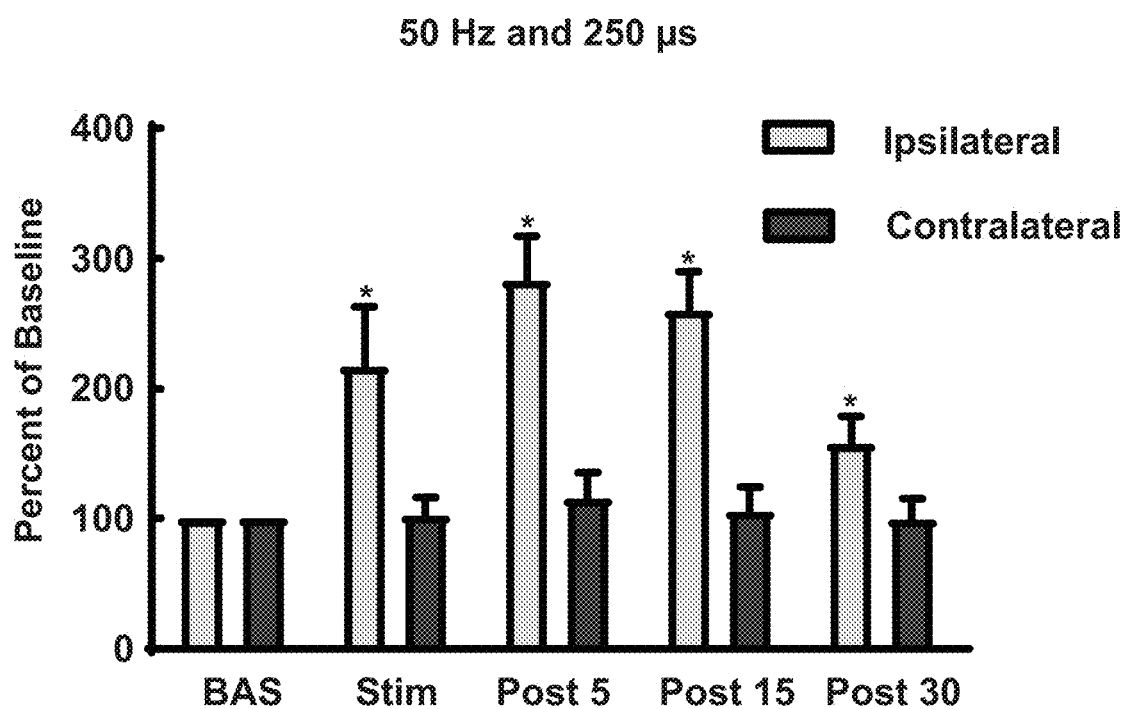
FIG. 13 is a chart illustrating example response data indicative of a patient response to therapy over time, in accordance with one or more of the various techniques disclosed herein.

FIG. 13 is a chart 1302 illustrating example response data indicative of a patient response to therapy over time, in accordance with one or more of the various techniques disclosed herein. FIG. 13 shows that SCS at parameters of 80-90% MT, 50 Hz, 250 μs significantly increased withdrawal thresholds during and after 10 minutes of stimulation (*$P<0.05$ vs. contralateral side). That is, processor 12 may determine an efficacy indicator corresponding to the particular set of stimulation parameters that signals an increase in withdrawal threshold when patient 52 receives SCS therapy at such SCS parameters defining low frequency or low energy SCS therapy.

According to the experimental study, a peroneal nerve injury was induced in four test subjects. QST was used to confirm the presence of hypersensitivity after injury. Test subjects were implanted with octopolar leads in the epidural space at the lumbar level of spinal cord 56.

A particular set of stimulation parameters (60 Hz, 200 μs PW, and an amplitude of 80-90% of MT) were tested to validate the model. Experimental testing of continuous stimulation at 500 Hz and 500 μs PW was conducted over 5 days at a lower amplitude of ($\leq$50% MT).

All test subjects with a peroneal nerve injury demonstrated hypersensitive behaviors (lower withdrawal thresholds). The hypersensitivity was sustained for at least one year and is ongoing (n=4, *$P<0.05$ vs. uninjured contralateral, side, FIG. 12). Application of SCS with low charge density and/or low frequency parameters (e.g., 80-90% MT, 50 Hz, 250 μs PW, for 10 minutes) was shown to increase the withdrawal thresholds (n=4, *$P<0.05$ vs. contralateral side) and had a carry-over effect (FIG. 13). When a greater charge (frequency and PW were increased to 500 Hz and 500 μs and amplitudes decreased to 50% MT) was tested, SCS produced a bi-phasic response, with an initial increase in withdrawal thresholds peaking after 10 minutes of stimulation and a second peak starting after 48 hours of continuous stimulation as compared to controls (n=4, *$P<0.05$ vs. baseline, † $P<0.05$ vs. contralateral side, ‡ $P<0.05$ vs. sham).

The experimental testing was carried out for particular substrates and materials, but it is recognized that similar solutions and systems can be applied to various materials.

Illustrative examples of the disclosure include:

Example 1

A method for providing therapy to a patient via electrical stimulation, the method comprising: determining, relative to a start time of providing the therapy, one or more efficacy times that correspond to an efficacy indicator; determining, according to the efficacy times, efficacy data items for the patient, the efficacy data items indicative of a response profile defined by one or more response variables; comparing the efficacy data items with the efficacy indicator; and generating, based on the comparison, a prediction of an expected response to the therapy manifesting in the patient at a prospective time.

Example 2

A method according to Example 1, wherein generating the prediction comprises: generating, based on the comparison, a probability function, wherein the probability function is indicative of a likelihood that the expected response to the electrical stimulation manifests in the patient at the prospective time; and outputting, based at least in part on the probability function, the expected response as comprising a long-term efficacy response to the therapy relative to the efficacy times.

Example 3

A method according to any of Examples 1 or 2, further comprising: determining, based on the prediction, an adjuster function; and applying the adjuster function to adjust the therapy in response to the prediction.

Example 4

A method according to any of Examples 1 through 3, wherein determining the one or more efficacy times comprises: determining a set of stimulation parameters that correspond to the therapy; and determining, based at least in part on the set of stimulation parameters, the one or more efficacy times.

Example 5

A method according to any of Examples 1 through 4, wherein the efficacy indicator indicates a plurality of expected pain relief values spanning a longer time window relative to a shorter time window of the response profile.

Example 6

A method according to any of Examples 1 through 5, wherein the efficacy indicator comprises one or more of: a predicted response profile, a set of response profile characteristics, or one or more response indicators.

Example 7

A method according to Example 6, wherein comparing the efficacy data items with the efficacy indicator comprises: correlating the efficacy data items to the predicted response profile to determine alignment of the efficacy data items with one or more portions of the predicted response profile that correspond to the efficacy times.

Example 8

A method according to any of Examples 1 through 7, wherein the efficacy data items comprise a first set of efficacy data items, and wherein the one or more efficacy times comprise a plurality of efficacy times, wherein generating the prediction comprises: determining a second set of efficacy data items for the patient, the second set of efficacy data items corresponding to an intermediate time that separates the plurality of efficacy times; correlating the second set of efficacy data items to the efficacy indicator to determine alignment of the second set of efficacy data items with an intermediate portion of the efficacy indicator that corresponds to the intermediate time; and determining, based at least in part on the correlation of the second set of efficacy items to the efficacy indicator, the prediction of the expected response.

Example 9

A method according to any of Examples 1 through 8, wherein the one or more efficacy times include: at least one first efficacy time in which a first response variable of the one or more response variables is expected to satisfy a first efficacy threshold, and at least one second efficacy time in which a second response variable of the one or more response variables is expected to satisfy a second efficacy threshold, wherein an amount of time separates the at least one first efficacy time and the at least one second efficacy time during which a third response variable is expected to reflect a lower pain relief value relative to pain relief values corresponding to the at least one first efficacy time or the at least one second efficacy time.

Example 10

A method according to any of Examples 1 through 9, wherein the efficacy indicator includes: a first set of expected efficacy metrics that define a first efficacy threshold, and a second set of expected efficacy metrics that comprise a difference amount relative to the first set of expected efficacy metrics, wherein the difference amount defines a second efficacy threshold, and wherein comparing the efficacy data items with the efficacy indicator comprises: comparing the efficacy data items with the first efficacy threshold or the second efficacy threshold, and wherein the generating the prediction comprises: determining, from the comparison, a proximity metric of the efficacy data items relative to the first efficacy threshold or the second efficacy threshold; and generating, based on the proximity metric, the prediction.

Example 11

A method according to any of Examples 1 through 10, wherein determining the efficacy data comprises: determine, via user input, pain relief values at the efficacy times; and storing the pain relief values of the patient with an indication as to when in time the pain relief values were determined relative to the start time of the therapy.

Example 12

A method according to any of Examples 1 through 11, wherein the one or more response variables correspond to one or more pain scores, wherein each pain score represents, in response to the therapy, a particular level of pain relief perceived by the patient.

Example 13

A method according to any of Examples 1 through 12, further comprising: delivering the electrical stimulation to the spinal cord of the patient for the treatment of pain.

Example 14

A system for providing therapy to a patient via electrical stimulation, the system comprising one or more means for performing the methods of any of Examples 1 through 13. For example, the system of Example 14 may include a memory configured to store an efficacy indicator including one or more efficacy times, the efficacy indicator corresponding to an electrical stimulation treatment for the patient; and one or more processors implemented in circuitry and in communication with the memory, the one or more processors configured to: identify a set of stimulation parameters defining the electrical stimulation treatment; determine, based at least in part on the set of stimulation parameters, the one or more efficacy times that correspond to the efficacy indicator; determine efficacy data items for the patient, the efficacy data items indicative of a response profile defined by one or more response variables, wherein the response profile corresponds to the one or more efficacy times; compare the efficacy data items with the efficacy indicator; and generate, based on the comparison, an efficacy prediction of long-term efficacy of the electrical stimulation treatment as indicated by an extrapolation of the response profile over time.

Example 15

A system according to Example 14, further wherein to generate the efficacy prediction, the one or more processors are configured to: generate, based on the comparison, a probability function, wherein the probability function is indicative of a likelihood of an expected response to the electrical stimulation treatment manifesting in the patient at a prospective time relative to a start time of a therapy program defining the electrical stimulation treatment; and output, based at least in part on the probability function, the efficacy prediction of the long-term efficacy.

Example 16

A system according to any of Examples 14 or 15, wherein the one or more processors are further configured to: determine, based on the efficacy prediction, an adjuster function; and apply the adjuster function to adjust the set of stimulation parameters in response to the efficacy prediction.

Example 17

A system according to any of Examples 14 through 16, wherein the efficacy data items comprise a first set of efficacy data items, and wherein the one or more efficacy times comprise a plurality of efficacy times, wherein to generate the efficacy prediction, the one or more processors are configured to: determine a second set of efficacy data items for the patient, the second set of efficacy data items corresponding to an intermediate time that separates the plurality of efficacy times; correlate the second set of efficacy data items to the efficacy indicator to determine alignment of the second set of efficacy data items with an intermediate portion of the efficacy indicator that corresponds to the intermediate time; and determine, based at least in part on the correlation of the second set of efficacy data items to the efficacy indicator and the correlation of the first set of efficacy items to the efficacy indicator, the efficacy prediction.

Example 18

A system according to any of Examples 14 through 17, wherein the efficacy indicator includes: a first set of expected efficacy metrics that satisfy a particular efficacy threshold, and a second set of expected efficacy metrics that comprise a difference amount relative to a value of the first set of expected efficacy metrics, wherein the difference amount satisfies a second efficacy threshold.

Example 19

A system according to any of Examples 14 through 18, wherein to determine the efficacy data items, the one or more processors are further configured to: output an indication of the one or more efficacy times; and receive, via user input, the efficacy data items in accordance with the one or more efficacy times.

Example 20

A system according to any of Examples 14 through 19, wherein to determine the one or more efficacy times, the one or more processors are configured to: determine an energy level corresponding to the set of stimulation parameters; and determine the one or more efficacy times based at least in part on the energy level.

Example 21

A system according to Example 20, wherein the efficacy data items comprise a first set of data items, and wherein the one or more processors are further configured to: determine a correlation between the first set of efficacy data items and the energy level; generate, based at least in part on the correlation, a baseline threshold level; determine a second set of efficacy data items; compare the second set of efficacy data items with the baseline threshold level; and generate an initial response indicator comprising a positive readout, wherein the positive readout indicates a probability of a positive response, wherein the probability satisfies a positive response threshold.

Example 22

A system according to any of Examples 14 through 21, wherein the one or more processors are further configured to: cause delivery of the electrical stimulation to the spinal cord of the patient for the treatment of pain.

In some implementations, the above-described examples 1-13 and/or 14-22 can be implemented using a computer-readable storage medium storing instructions that when executed cause one or more processors of a system to perform some or all of the various operations. For example, a computer-readable storage medium can be provided storing instructions that when executed cause one or more processors of a system for providing therapy to a patient via electrical stimulation to: identify a set of stimulation parameters defining an electrical stimulation treatment for a patient; determine, based at least in part on the set of stimulation parameters, one or more efficacy times that correspond to an efficacy indicator; determine, at the efficacy times, efficacy data items for the patient, the efficacy data items indicative of a response profile defined by one or more response variables; compare the efficacy data items with the efficacy indicator; and generate, based on the comparison, a prediction of the electrical stimulation treatment invoking an expected response in the patient over time relative to a start time of the electrical stimulation treatment.

In some implementations, the above-described examples 1-13 and/or 14-22 can be implemented using an apparatus comprising one or more means for performing some or all of the various operations. For example, an apparatus for providing therapy to a patient via electrical stimulation includes: means for determining, relative to a start time of providing the therapy, one or more efficacy times that correspond to an efficacy indicator; means for determining, according to the efficacy times, efficacy data items for the patient, the efficacy data items indicative of a response profile defined by one or more response variables; means for comparing the efficacy data items with the efficacy indicator; and means for generating, based on the comparison, a prediction of an expected response to the therapy manifesting in the patient at a prospective time.

Example 21

A system, device, or method consistent with any example discussed herein.

Example 22

A system, device, or method for providing a long-term therapy efficacy prediction based upon a short-term response profile.

Based upon the above discussion and illustrations, it is recognized that various modifications and changes may be made to the disclosed technology in a manner that does not necessarily require strict adherence to the examples and applications illustrated and described herein. Such modifications do not depart from the true spirit and scope of various aspects of the disclosure, including aspects set forth in the claims.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in the disclosure. A computer program product may include a computer-readable medium.

By way of example, and not limitation, such computer-readable data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Combinations of the above should also be included within the scope of computer-readable media.

Instructions may be executed by one or more processors, such as one or more DSPs, general purpose microprocessors, ASICs, FPGAs, complex programmable logic devices (CPLDs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Any of the above-mentioned "processors," and/or devices incorporating any of the above-mentioned processors or processing circuitry, may, in some instances, be referred to herein as, for example, "computers," "computer devices," "computing devices," "hardware computing devices," "hardware processors," "processing units," "processing circuitry," etc. Computing devices of the above examples may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In some examples, the computing devices may be controlled by a proprietary operating system. Conventional operating systems control and schedule computer processes for execution, perform memory management, provide file system, networking, input/output (I/O) services, and provide UI functionality, such as graphical user interface ("GUI") functionality, among other things.

The techniques of the disclosure may be implemented in a wide variety of devices or apparatuses, including an integrated circuit (IC) or a set of ICs (e.g., a chip set). Various components, modules, or units are described in the disclosure to emphasize functional aspects of devices configured to perform the disclosed techniques, but do not necessarily require realization by different hardware units.

Various examples have been described. These and other examples are within the scope of the following claims.

What is claimed is:

1. A method for providing therapy to a patient via electrical stimulation, the method comprising:
   determining, relative to a start time of providing the therapy, one or more efficacy times that correspond to an efficacy indicator, wherein determining the one or more efficacy times comprises:
      determining a set of stimulation parameters that correspond to the therapy; and
      determining, based at least in part on the set of stimulation parameters, the one or more efficacy times;
   determining, according to the efficacy times, efficacy data items for the patient, the efficacy data items indicative of a response profile defined by one or more response variables;
   comparing the efficacy data items with the efficacy indicator; and
   generating, based on the comparison, a prediction of an expected response to the therapy manifesting in the patient at a prospective time.

2. The method of claim 1, wherein generating the prediction comprises:
   generating, based on the comparison, a probability function, wherein the probability function is indicative of a likelihood that the expected response to the electrical stimulation manifests in the patient at the prospective time; and
   outputting, based at least in part on the probability function, the expected response as comprising a long-term efficacy response to the therapy relative to the efficacy times.

3. The method of claim 1, further comprising:
   determining, based on the prediction, an adjuster function; and
   applying the adjuster function to adjust the therapy in response to the prediction.

4. The method of claim 1, wherein the efficacy indicator indicates a plurality of expected pain relief values spanning a longer time window relative to a shorter time window of the response profile.

5. The method of claim 1, wherein the efficacy indicator comprises one or more of: a predicted response profile, a set of response profile characteristics, or one or more response indicators.

6. The method of claim 5, wherein comparing the efficacy data items with the efficacy indicator comprises:
   correlating the efficacy data items to the predicted response profile to determine alignment of the efficacy data items with one or more portions of the predicted response profile that correspond to the efficacy times.

7. The method of claim 1, wherein the efficacy data items comprise a first set of efficacy data items, and wherein the one or more efficacy times comprise a plurality of efficacy times, wherein generating the prediction comprises:
   determining a second set of efficacy data items for the patient, the second set of efficacy data items corresponding to an intermediate time that separates the plurality of efficacy times;
   correlating the second set of efficacy data items to the efficacy indicator to determine alignment of the second set of efficacy data items with an intermediate portion of the efficacy indicator that corresponds to the intermediate time; and
   determining, based at least in part on the correlation of the second set of efficacy items to the efficacy indicator, the prediction of the expected response.

8. The method of claim 1, wherein the one or more efficacy times include:
   at least one first efficacy time in which a first response variable of the one or more response variables is expected to satisfy a first efficacy threshold, and
   at least one second efficacy time in which a second response variable of the one or more response variables is expected to satisfy a second efficacy threshold,
   wherein an amount of time separates the at least one first efficacy time and the at least one second efficacy time during which a third response variable is expected to reflect a lower pain relief value relative to pain relief values corresponding to the at least one first efficacy time or the at least one second efficacy time.

9. The method of claim 1,
   wherein the efficacy indicator includes: a first set of expected efficacy metrics that define a first efficacy threshold, and a second set of expected efficacy metrics that comprise a difference amount relative to the first set of expected efficacy metrics, wherein the difference amount defines a second efficacy threshold, and
   wherein comparing the efficacy data items with the efficacy indicator comprises:
      comparing the efficacy data items with the first efficacy threshold or the second efficacy threshold, and
   wherein generating the prediction comprises:
      determining, from the comparison, a proximity metric of the efficacy data items relative to the first efficacy threshold or the second efficacy threshold; and
      generating the prediction based on the proximity metric.

10. The method of claim 1, wherein determining the efficacy data comprises:
    determining, via user input, pain relief values at the efficacy times; and
    storing the pain relief values of the patient with an indication as to when in time the pain relief values were determined relative to the start time of the therapy.

11. The method of claim 1, wherein the one or more response variables correspond to one or more pain scores, wherein each pain score represents, in response to the therapy, a particular level of pain relief perceived by the patient.

12. A system for providing therapy to a patient via electrical stimulation, the system comprising:
    a memory configured to store an efficacy indicator including one or more efficacy times, the efficacy indicator corresponding to an electrical stimulation treatment for the patient; and
    one or more processors in communication with the memory, the one or more processors configured to:
       identify a set of stimulation parameters defining the electrical stimulation treatment;
       determine, based at least in part on the set of stimulation parameters, the one or more efficacy times that correspond to the efficacy indicator;
       determine efficacy data items for the patient, the efficacy data items indicative of a response profile defined by one or more response variables, wherein the response profile corresponds to the one or more efficacy times, wherein to determine the efficacy data items, the one or more processors are further configured to receive, via user input, the efficacy data items in accordance with the one or more efficacy times;
       compare the efficacy data items with the efficacy indicator; and generate, based on the comparison, an efficacy prediction of long-term efficacy of the electrical stimulation treatment as indicated by an extrapolation of the response profile over time.

13. The system of claim 12, wherein to generate the efficacy prediction, the one or more processors are configured to:
generate, based on the comparison, a probability function, wherein the probability function is indicative of a likelihood of an expected response to the electrical stimulation treatment manifesting in the patient at a prospective time relative to a start time of a therapy program defining the electrical stimulation treatment; and
output, based at least in part on the probability function, the efficacy prediction of the long-term efficacy.

14. The system of claim 12, wherein the one or more processors are further configured to:
determine, based on the efficacy prediction, an adjuster function; and
apply the adjuster function to adjust the set of stimulation parameters in response to the efficacy prediction.

15. The system of claim 12, wherein the efficacy data items comprise a first set of efficacy data items, and wherein the one or more efficacy times comprise a plurality of efficacy times, wherein to generate the efficacy prediction, the one or more processors are configured to:
determine a second set of efficacy data items for the patient, the second set of efficacy data items corresponding to an intermediate time that separates the plurality of efficacy times;
correlate the second set of efficacy data items to the efficacy indicator to determine alignment of the second set of efficacy data items with an intermediate portion of the efficacy indicator that corresponds to the intermediate time; and
determine the efficacy prediction based at least in part on the correlation of the second set of efficacy data items to the efficacy indicator and the correlation of the first set of efficacy items to the efficacy indicator.

16. The system of claim 12, wherein to determine the efficacy data items, the one or more processors are further configured to:
output an indication of the one or more efficacy times.

17. The system of claim 12, wherein to determine the one or more efficacy times, the one or more processors are configured to:
determine an energy level corresponding to the set of stimulation parameters; and
determine the one or more efficacy times based at least in part on the energy level.

18. The system of claim 17, wherein the efficacy data items comprise a first set of data items, and wherein the one or more processors are further configured to:
determine a correlation between the first set of efficacy data items and the energy level;
generate, based at least in part on the correlation, a baseline threshold level;
determine a second set of efficacy data items;
compare the second set of efficacy data items with the baseline threshold level; and
generate an initial response indicator comprising a positive readout, wherein the positive readout indicates a probability of a positive response, wherein the probability satisfies a positive response threshold.

19. A non-transitory computer-readable storage medium having stored thereon instructions that, when executed, cause one or more processors to at least:
identify a set of stimulation parameters defining an electrical stimulation treatment for a patient;
determine, based at least in part on the set of stimulation parameters, one or more efficacy times that correspond to an efficacy indicator;
determine, at the efficacy times, efficacy data items for the patient, the efficacy data items indicative of a response profile defined by one or more response variables, wherein the one or more response variables correspond to one or more pain scores, wherein each pain score represents, in response to the therapy, a particular level of pain relief perceived by the patient;
compare the efficacy data items with the efficacy indicator; and
generate, based on the comparison, a prediction of the electrical stimulation treatment invoking an expected response in the patient over time relative to a start time of the electrical stimulation treatment.

* * * * *